(12) United States Patent
Smith et al.

(10) Patent No.: US 7,723,085 B2
(45) Date of Patent: May 25, 2010

(54) ANALYZING CELLS IMMOBILIZED IN BLOCK COPOLYMERS

(75) Inventors: Paul Smith, Craig Penllyn (GB); Laurence Patterson, Shepshed (GB); Rachel Jane Errington, Abbey Meads (GB)

(73) Assignee: Biostatus Limited (GB)

( * ) Notice: Subject to any disclaimer, the term of this patent is extended or adjusted under 35 U.S.C. 154(b) by 316 days.

(21) Appl. No.: 11/571,559

(22) PCT Filed: Jul. 1, 2005

(86) PCT No.: PCT/GB2005/002603

§ 371 (c)(1),
(2), (4) Date: Jun. 28, 2007

(87) PCT Pub. No.: WO2006/003423

PCT Pub. Date: Jan. 12, 2006

(65) Prior Publication Data

US 2008/0182287 A1    Jul. 31, 2008

(30) Foreign Application Priority Data

Jul. 2, 2004  (GB) ................................ 0414825.0

(51) Int. Cl.
*C12N 11/02* (2006.01)
(52) U.S. Cl. ...................................... 435/177; 435/180
(58) Field of Classification Search .................. 435/117, 435/180
See application file for complete search history.

(56) References Cited

U.S. PATENT DOCUMENTS

| | | | |
|---|---|---|---|
| 5,628,981 A | 5/1997 | Liversidge et al. | |
| 6,171,825 B1 | 1/2001 | Chan et al. | |
| 7,452,565 B2* | 11/2008 | Banerjee et al. | 427/2.1 |
| 2004/0033598 A1* | 2/2004 | Vacanti et al. | |
| 2008/0160501 A1* | 7/2008 | Hammond et al. | 435/4 |

OTHER PUBLICATIONS

Dulbecco and Vogt, "Plaque formation and isolation of pure lines with Poliomyelitis viruses", *J. Exp. Med.*, 99(2):167-82 (1954).
Errington and White, "Measuring dynamic cell volume in situ by confocal microscopy", *Methods Mol. Biol.*, 122:315-40 (1999).
http://www.dtp.nci.nih.gov/docs/misc/common_files/cell_list.html.
http://patft.uspto.gov.netacgi/nph-Parser?Sect1=PTO&Sect2=HITOFF&p=1&u=/netahtml/search-bool.html&r=1&f=G&l=50&co=AND&d=ptxts1=LIVERSIDGE.INZZ.
&s2=EICKHOFF.INZZ.&OS=    IN/LIVERSIDGE+ANS+IN/EICKHOFF&RS=IN/LIVERSIDGE+AND+IN/EICKHOFF.
http://www.biostatus.co.uk/cygel_features.html.
http://www.biostatus.co.uk/cygel_applications.html.
http://www.biostatus.co.uk/cygel_applications_2.html.
http://www.biostatus.co.uk/cygel_msds.html.
http://www.biostatus.co.uk/cygel_technical_1.html.
http://www.biostatus.co.uk/cygel_technical_2.html.
http://www.biostatus.co.uk/cygel_applications_3.html.
http://www.biostatus.co.uk/cygel_applications_4.html.
http://www.availabletechnologies.pnl.gov/biomedical/rev.stm.
http://www.availabletechnologies.pnl.gov/biomedical/rever.stm.
Kabanov, et al., "Pluronic block copolymers as novel polymer therapeutics for drug and gene delivery", *J. Control Release*, 82(2-3):189-212 (2002).
MacGregor, "Ph.D. Thesis: Design and in vitro cytotoxicity evaluation of a thermoreversible gel for the topical delivery of anticancer drugs", DeMontfort University (1994).
Negulescu and Machen, "Intracellular ion activities and membrane transport in parietal cells measured with fluorescent dyes", *Methods Enzymol.*, 192:38-81 (1990).
Saim, et al., "Engineering autogenous cartilage in the shape of a helix using an injectable hydrogel scaffold", *Laryngoscope*, 110(10 Pt 1):1694-7 (2000).
Schmolka, "Artificial skin I. Preparation and properties of Pluronic® F-127 gels for treatment of burns", *J. Biomed. Mater. Res.*, 6(6):571-582 (1972).
Smolewski, et al., "'Liquidless' cell staining by dye diffusion from gels and analysis by laser scanning cytometry: potential application at microgravity conditions in space", *Cytometry*, 44(4):355-60 (2001).
White and Errington, "Fluorescence techniques for drug delivery research: theory and practice", *Adv. Drug Deliv. Rev.*, 57(1):17-42 (2005).
Zahn, et al., "Fluorimetric multiparameter cell assay at the single cell level fabricated by optical tweezers", *FEBS Lett.*, 443(3):337-40 (1999).

* cited by examiner

*Primary Examiner*—Ralph Gitomer
(74) *Attorney, Agent, or Firm*—Pabst Patent Group LLP

(57) ABSTRACT

The present invention provides the use of a composition comprising a block polymer as a support matrix in the manipulation, processing or analysis of particles, such as cells and fluorescent beads. In a preferred embodiment, the composition exhibits gel-sol thermoreversibility, micelle formation under gelling conditions, optically compatible, controllable surfactant properties, molecular sieving properties and biocompatibility. Further aspects of the invention provide (a) a support matrix composition comprising a block polymer, fluorescent beads and/or a dye for use in the manipulation, processing or analysis of particles, (b) a multichamber plate coated in a support matrix composition and (c) kits for producing the same.

28 Claims, 15 Drawing Sheets

Panels a-k: Slide preparation protocol

Panels l & m: Well preparation protocol

US 7,723,085 B2

ANALYZING CELLS IMMOBILIZED IN BLOCK COPOLYMERS

CROSS REFERENCE TO RELATED APPLICATIONS

This application is a filing under 35 U.S.C. §371 of PCT/GB2005/002603 filed with the Great Britain Receiving Office of the Patent Cooperation Treaty on Jul. 1, 2005, which claims the benefit of British Patent Application No. GB 0414825.0, which was filed with the British Patent Office on Jul. 2, 2004.

FIELD OF THE INVENTION

The invention relates to thermoreversible gel compositions and their applications generally in research, diagnostic and screening assays and methodology in the use of a cell- or particle- or reagent-support matrix based applications.

BACKGROUND OF THE INVENTION

There exists a need to make biological assays faster and simpler to perform with an overriding drive to make the processes cheaper yet maintain accuracy and reproducibility. This is due to a rapid increase in the number of research and diagnostic molecular probes available (e.g. new fluorescent reporter molecules) and the advantages in terms of information content of multiplexing such assays across a range of instruments. Increasingly there is a need for cell-, particle- and bead-based (and a combination of these units) assays in which the presence, for example, of cells with certain features indicates disease processes. Similarly, the demand and evolution of rational approaches in the search for bioactive molecules for new medicines has resulted in a need for low cost high-through-put screening (HTS) and the development of cell- and molecule-based assays, tools and arrays within the field of functional analysis.

Such assays require or are enhanced by the availability of methodologies for:
i) the manipulation of cells/particles, analytes and reagents in liquid and gel phases for processing purposes,
ii) the controlled delivery of fluorescent/bioluminescent molecules to cells/particles or the retention of the fluorescent/bioluminescent-associated properties of said particle/cells.
iii) the controllable immobilisation of said cells/particles for the purpose of analysis involving light collection
iv) the retention of cell viability and cell function for periods of time sufficient for the purposes of an analysis.

The present invention seeks to provide means for use in such methodologies.

A variety of hydrogels based upon thermoreversible polymers (in liquid form at elevated temperatures but in gel form at lower temperatures) are known, including natural gel-forming materials such as agarose, agar, furcellaran, beta-carrageenan, beta-1,3-glucans such as curdlan, gelatin, or polyoxyalkylene containing compounds.

The present invention exploits to the distinct advantages and properties of block polymer-based gels, such as polyoxypropylene-polyoxyethylene block polymer gels (PBP), which unusually undergo transition to liquid form upon temperature reduction. This property can be described as 'reversed thermosetting'.

Selected properties of the PBP preparations, such as detergent properties and the mechanical and thermoreversible properties of hydrogels in general, have been documented and exploited in the art.

For example, reported uses and properties of PBP preparations include the following:

Surfactant Properties

Polyoxypropylene-polyoxyethylene block polymer (PBP) has been used as a non-ionic surfactant for detergents, dispersants, binders, stabilisers, defoaming agents, emulsifying agents to name but a few. At high aqueous PBP concentrations, beyond a transition temperature, a gel can form comprising amphiphilic block copolymer micelles. A commercial Pluronic® preparation F-127 ($PEO_{99}$-$PPO_{69}$-$PEO_{99}$, with E and P being polyoxyethylene and polyoxypropylene, respectively) has been used in gel form for pharmaceutical preparations.

Reverse Agar and Biofilms

Gel-forming formulations of PBP have been described as 'reverse agar' in their use. The low temperature gelling formulation has been used to support the limited growth of micro-organisms in conventional microbiology applications. Such Pluronic®-based hydrogels have been used extensively to assay biocide treatments. Gel-trapped micro-organism populations mimic the localized high cell densities observed in biofilms and are subject to the similar nutrient and chemical gradients found within natural biofilms. Such prior art uses with respect to micro-organisms has revealed that PBP should have low toxicity in the stable gel form.

Molecular Sieve Properties

PBP gel form has the potential to form ordered micellar structures and has been used as a separation media for nucleic acids, indicating the coherent movement of molecules through the gel upon the passage of a continuous or pulsed electrical current. Microdevices have also been designed with sieving gels within the same device to perform separations involving both single- and double-stranded DNA over distances on the order of 1 cm. Extensive comparisons have been made to compare different gel matrices on the basis of gel casting ease, reusability, and overall separation performance using for example a 100 base pair double-stranded DNA ladder as a standard sample.

Hydropads

Miniature size and high sensitivity of biochips is sought in diagnostics, testing, and research in medicine, veterinary science and applications, agriculture, toxicology, environmental monitoring, forensics etc. Three dimensional biochips comprising non-thermoreversible gels (hydropads) have been developed consisting of an array of three-dimensional gel elements on the hydrophobic surface of a microscope slide. For example, a gel-based biochip project was initiated in Engelhardt Institute of Molecular Biology of the Russian Academy of Science (EIMB) in 1989 resulting in the development of the 'Immobilized Micro Array of Gel Elements' on chip (or IMAGE chip), which can bear oligonucleotides, DNA, proteins, small compounds or cells fixed within semi spherical hydrogel pads. A simple two-step procedure has been developed for the large-scale manufacture of such chips. The gel pads can serve both as support for immobilisation and as individual nanoliter test tubes to carry out various specific interactions, chemical or enzymatic reactions. Chips have been produced that contain immobilized antibodies, antigens, enzymes, receptors, and different ligands.

Cell Encapsulation

Polymeric gels have also been explored as cell encapsulation materials for tissue engineering. Isolated mammalian cells and tissues have countless applications in medicine and biotechnology, yet protecting and nourishing cells either in vitro or in vivo while harvesting the desired products has proven difficult.

Drug and Dye Delivery

Previous clinical applications have revealed the use of hydrogels for the purpose of local delivery of pharmacologically active agents to tissues. In contrast, previous work on the "liquid less" cell staining by dye diffusion from gels (polyacrylamide or gelatin) has been restricted to the use of gel systems lacking the unique thermoreversible properties of PBP-based gels. Such studies have been described by Smolweski et al., 2001, *Cytometry* 44(4):355-60. Dye delivery to cells was observed but required a 2- to 4-fold increase in normal staining concentration of DNA dyes.

SUMMARY OF THE INVENTION

The present invention provides for a general means of combining the four methodologies stated above by exploiting the features of block polymer (for example, based on polyoxypropylene-polyoxyethylene block polymer [PBP]) gels namely the thermoreversible (gel-sol transition enabling manipulation; as defined below) properties, micelle formation under gelling conditions (enabling the gel to act as a support/immobilizing matrix), optical properties (low absorbance and non-fluorescent enabling light-based optical analyses), controllable surfactant properties (enabling modified reporter molecule delivery to cells and a means of cell solubilisation), molecular sieving properties (providing controlled, i.e. modified and regulated, delivery of exogenous reporter molecules) and low toxicity (enabling live cell processing). The invention also provides for a general means of making assays modular by enabling the control and manipulation of cells/particles and regulating reactant and reporter molecule access for use in such cell-based assays. Specific formulations of PBP gels would provide optimal performance for a given application or excipient property.

By 'thermoreversible' we refer to the property of gel formation upon raising the temperature of a PBP composition above a critical transition point while a liquid or sol form of the composition exists at temperatures below that transition point.

The current invention provides means for the recovery of test inoculums without further trauma and the use of gel in eukaryotic systems (e.g. human and animal cells).

The molecular sieving property of block polymer gels provides a means of the coherent delivery and behaviour of analytes (such as molecular reporter molecules) for the purpose of sequential or controlled delivery to a system under analysis.

Thermoreversible gelling properties of block polymer gels also avoids thermal damage thus providing an advantageous route for cell harvesting and recovery. One strategy is to encapsulate cells in a matrix that allows for the diffusion of small molecules to and from cells. Encapsulation offers promising results, since PBP polymers are often biocompatible and provide a three-dimensional scaffolding for the simulation of support conditions in multicellular systems. To some extent the success of cellular encapsulation depends on the cell type. The purpose of the gel is to provide a matrix-gel environment, which allows cells, isolated from different tissue to maintain their original cellular phenotype. In an ideal situation the gel should provide an inert environment (i.e. it does not act to stimulate or activate cells to do something abnormal). The cells placed in such gels are able to function normally and perhaps overtime organize the gel with the synthesis of secreted macromolecules to form pseudo-tissue explants. The current invention incorporates all of the required features of a cell encapsulation matrix. It allows cells to be incorporated whilst the PBP gel is in liquid form. Upon gel formation the cells become trapped. It is possible to administer the necessary reagents whilst the gel is in either phase thus ensuring the cells are able to absorb the necessary agents whilst in a supported environment. The gel with the trapped cells can be placed at a lower temperature thus allowing the cells to be extracted by transition to the liquid phase even from selected regions of the gel thereby permitting micro-selection of cell populations with given characteristics without any adverse effects. The same applies to any particle fixed in this way.

Potential advantages of block polymer gels for dye delivery include their utility in microgravity conditions and conditions where spillage is not desirable. Thermoreversible PBP preparations containing potentially hazardous excipients (e.g. mutagenic dyes) would have the additional safety feature of forming a gel at skin temperatures and above thereby, reducing diffusion-limited transdermal delivery. The safe delivery of dye molecules can provide access to a wider range of applications and excipients. The present invention also allows for the solid-phasing of dye delivery systems with significant safety advantages and for the cold formulation of preparations with thermolabile excipients.

Thus, a first aspect of the invention provides the use of a composition comprising a block polymer as a support matrix in the manipulation, processing or analysis of particles. In particular, the invention provides the use of a composition comprising a block polymer as a support matrix in the optical analysis of particles.

The block polymer composition is not used merely as a substrate or medium for cell culture.

Preferably, the support matrix exhibits the following properties:

1. gel-sol thermoreversibility;
2. micelle formation under gelling conditions;
3. optical compatibility (i.e. compatible with light-based optical assays; electromagnetic spectrum 350 to 1300 nm);
4. controllable surfactant properties;
5. molecular sieving properties; and
6. biocompatibility.

It will be appreciated by persons skilled in the art that the block polymer composition may be used as a support matrix for any particulate matter.

In a preferred embodiment, the particles are derived from or constitute a biological sample. Preferably, the particles are cells, for example fixed or live prokaryotic or eukaryotic cells. The cells may be adherent or non-adherent.

Advantageously, the cells are selected from the group consisting of the following cell types:

1. Animal cells including human and mammalian cells derived as biopsy specimens (e.g. by fine needle aspirates), as tissue explants, as primary cultures (e.g. human skin fibroblasts), as transformed cell lines (e.g. Epstein Barr virus transformed lymphoblasts), as immortalized cell lines (e.g. cell lines immortalized with human telomerase reverse transcriptase [hTERT]), and as established tumour cell lines.
2. Human tumour cell lines including those representing specific sites and diseases of therapeutic, diagnostic and analytical interest, for example: Brain Cancer, Bladder Cancer, Breast Cancer, Colon and Rectal Cancer, Endometrial Cancer, Kidney Cancer (Renal Cell), Leukemia, Lung Cancer, Melanoma, Non-Hodgkin's Lymphoma, Pancreatic Cancer, Prostate Cancer, Skin Cancer (Non-melanoma), Thyroid Cancer.
3. Cell lines with adherent (e.g. breast cancer cell lines MCF-7) or non-adherent (e.g. the leukemia cell line CCRF-CEM or the classical small cell lung carcinoma cell line NCI-H69) properties.
4. Mammalian cell lines used in functional genomics studies (e.g. NIH 3T3 murine cell line)
5. Human tumour cells cell lines available for the purpose of drug screening methodologies such as those indicated in the U.S. National Cancer Institute tumour cell line panel (ref: http://dtp.nci.nih.gov/docs/misc/common_files/cell_list.html), comprising but not limited to: CCRF-CEM, HL-60(TB), K-562, MOLT-4, RPMI-8226, SR, A549/ATCC, EKVX, HOP-62, HOP-92, NCI-H226, NCI-H23, NCI-H322M, NCI-H460, NCI-H522, COLO 205, HCC-2998, HCT-116, HCT-15, HT29, KM12, SW-620, SF-268, SF-295, SF-539, SNB-19, SNB-75, U251, LOX IMVI, MALME-3M, M14, SK-MEL-2, SK-MEL-28, SK-MEL-5, UACC-257, UACC-62, IGR-OV1, OVCAR-3, OVCAR-4, OVCAR-5, OVCAR-8, SK-OV-3, 786-0, A498, ACHN, CAKI-1, RXF 393, SN12C, TK-10, UO-31, PC-3, DU-145, MCF7, NCI/ADR-RES, MDA-MB-231/ATCC, HS 578T, MDA-MB-435, MDA-N, BT-549, T-47D, LXFL 529, DMS 114, SHP-77, DLD-1, KM20L2, SNB-78, XF 498, RPMI-7951, M19-MEL, RXF-631, SN12K1, MDA-MB-468, P388, P388/ADR.
6. Human tumour cell lines selected for their functional expression of specific molecular entities such as transporters of xenobiotic molecules (e.g. the ABCA3 drug transporter expressing in lung cancer lines H522M, A549, and EKVX).
7. Human tumour cells select for their convenient performance in gene transfer studies (e.g. U2-OS human osteosarcoma cells).
8. Single- and multi-cellular forms of vertebrates (e.g. embryos, larval forms or derived dissociated cell preparations of zebrafish Danio [Brachydanio] rerio).
9. Cell lines used in ADME/Tox (Absorption, Distribution, Metabolism, Elimination/Toxicity) screening protocols (e.g. hepatocyte derived cell lines such as HepG2).
10. Embryonic stem cells derived from human or murine sources.
11. Neurones and/or supporting cells of the central nervous system (e.g. astrocytes, oligodendrocytes, microglia and Schwann cells).
12. Immortal somatic cell hybrids including hybrids that secrete antibodies (e.g. hybridomas)
13. Yeasts (e.g. Saccharomyces cerevisiae and Schizosaccharomyces pombe)
14. Cells derived from plants (e.g. for the analysis of in vitro propagation methodologies for new cultivars, rare species, and difficult-to-propagate plants).
15. Immune response cells (e.g. antigen presenting dendritic cells)
16. Extra- and intra-cellular forms of animal parasites (e.g. Plasmodium falciparum).
17. Micro-organisms including pathogenic bacteria of diagnostic interest (e.g. Methicillin-resistant Staphylococcus aureus).
18. Fungi including those used in pest-control (e.g. Entomopathogenic fungi including the genera Beauveria, Metarhizium and Tolypocladium).
19. Single and multicellular forms of free-living animals such the nematode Caenorhabditis elegans.
20. Cells derived from organotypic cultures (e.g. cell clumps, spheroids and brain slices).
21. Cells derived from explant material (e.g. cartilage, skin and invertebral disc).

Conveniently, the cells are capable of expressing a fluorescent molecule. For example, the cells may be engineered by recombinant DNA techniques to express green fluorescent protein (GFP) and/or spectral variants and/or stability variants thereof.

Preferably, the composition provides an inert environment for cells. More preferably, the composition is sterile prior to use.

In an alternative preferred embodiment, the particles are fluorescent beads. Such beads may provide a particle for calibration that has a specific size (large up to 30 μm and sub-resolution, e.g. below 200 nm), fixed amount of fluorophore, unique fluorophore spectra and mixtures thereof. Suitable beads are available from Molecular Probes (Invitrogen), Carlsbad, US (e.g. FluoSpheres™).

Advantageously, the composition enables particles to be immobilised therein.

It will be appreciated by persons skilled in the art that the block polymer composition for use in the present invention must exhibit gel-sol thermoreversibility. Preferably, the composition comprises a block copolymer of polyoxyethylene and polyoxypropylene, such as a poloxamer.

Poloxamers are polyethylene-polypropylene glycol block polymers containing ethylene oxide (PEO) and propylene oxide (PPO) moles according to the formula (See Table 1):

(PEO).sub.a-(PPO).sub.b-(PEO).sub.c.

TABLE 1

Molecular Weights of Poloxamers

| Poloxamer No. | Pluronic ® | Av. Mol. Wt | Av. Values | | |
|---|---|---|---|---|---|
| | | | a | b | c |
| 401 | | 4,400 | 6 | 67 | 6 |
| 402 | | 5,000 | 13 | 67 | 13 |
| 403 | | 5,750 | 21 | 67 | 21 |
| 407 | F127 | 12,000 | 98 | 67 | 98 |
| 331 | | 3,800 | 7 | 54 | 7 |
| 333 | | 4,950 | 20 | 54 | 20 |
| 334 | | 5,850 | 31 | 54 | 31 |
| 335 | | 6,000 | 38 | 54 | 38 |
| 338 | F108 | 15,000 | 128 | 54 | 128 |
| 282 | | 3,650 | 10 | 47 | 10 |
| 284 | | 4,600 | 21 | 47 | 21 |
| 288 | F98 | 13,500 | 122 | 47 | 122 |
| 231 | | 2,750 | 6 | 39 | 6 |
| 234 | | 4,200 | 22 | 39 | 22 |
| 235 | | 4,600 | 27 | 39 | 27 |
| 237 | F87 | 7,700 | 62 | 39 | 62 |
| 238 | F88 | 10,800 | 97 | 39 | 97 |
| 212 | | 2,750 | 8 | 35 | 8 |
| 215 | | 4,150 | 24 | 35 | 24 |
| 217 | F77 | 6,600 | 52 | 35 | 52 |
| 181 | | 2,000 | 3 | 30 | 3 |
| 182 | | 2,500 | 8 | 30 | 8 |
| 183 | | 2,650 | 10 | 30 | 10 |
| 184 | | 2,900 | 13 | 30 | 13 |
| 185 | | 3,400 | 19 | 30 | 19 |
| 188 | F68 | 8,350 | 75 | 30 | 75 |
| 122 | | 1,630 | 5 | 21 | 5 |
| 123 | | 1,850 | 7 | 21 | 7 |
| 124 | | 2,200 | 11 | 21 | 11 |
| 101 | | 1,100 | 2 | 16 | 2 |
| 105 | | 1,900 | 11 | 16 | 11 |
| 108 | F38 | 5,000 | 46 | 16 | 46 |

Certain number of the above poloxamers are also known as Pluronic ®, which is a brand name of BASF Corporation.

Preferred are poloxamers wherein;
a is 46 to 128;
b is 16 to 67; and
c is 46 to 128.

More preferred are poloxamers wherein;
a is 46, 52, 62, 75, 97, 98, 122 and 128;
b is 16, 30, 35, 39, 47, 54 and 67; and
c is 46, 52, 62, 75, 97, 98, 122 and 128.

Most preferably, the block polymer is selected from the following poloxamers with recognized capacity to form gels (see http://www.basf.com/static/OpenMarket/Xcelerate/Preview_cid-982931200587_pubid-974236729499_c-Article-.html):

| Generic name | Proprietary name |
| --- | --- |
| Poloxamer 407 | Pluronic ® F127 |
| Poloxamer 338 | Pluronic ® F108 |
| Poloxamer 288 | Pluronic ® F98 |
| Poloxamer 237 | Pluronic ® F87 |
| Poloxamer 238 | Pluronic ® F88 |
| Poloxamer 217 | Pluronic ® F77 |
| Poloxamer 188 | Pluronic ® F68 |
| Poloxamer 108 | Pluronic ® F38 |

In a particularly preferred embodiment, the block polymer is poloxamer 407 (Pluronic® F127, BASF).

The block polymer may be prepared in any suitable aqueous medium. For example, the block polymer is prepared in distilled water or a physiological buffer, such as phosphate-buffered saline (PBS).

Preferably, the composition has a pH of 7.2 to 7.4.

It will be appreciated that the block polymer should be present in the support matrix composition at a gelling concentration. In a preferred embodiment, the block polymer is present in the composition at a concentration of 24% (w/v).

Advantageously, the composition is in a liquid (sol) form under chilled conditions (for example, 0 to 5° C.) and yet in a semi-solid gel form at room temperatures and above. For example, the composition may achieve a gel form at a transition temperature between room temperature and 37° C.

It will be appreciated that the transition temperature of the composition may be modified by altering the formulation of the composition, for example by changing the concentration of the block polymer in the composition. Alternatively, the transition temperature of the block polymer composition may be modified by the addition of one or more excipients, examples of which are given in Table 2.

TABLE 2

Effect of specific additives on the sol-gel transition temperature for a 24% w/v preparation of Polyoxypropylene-Polyoxyethylene Block Polymer (PBP) 407.

| Additive | Effect on transition temperature (° C.) |
| --- | --- |
| 1% w/v sorbitol | −1.4 |
| 5% w/v sorbitol | −3.0 |
| 1% w/v hydroxyethylcellulose | −0.3 |
| 5% w/v hydroxyethylcellulose | −2.2 |
| 1% w/v glycerol | −0.2 |
| 5% w/v glycerol | −2.4 |
| 1% w/v sodium chloride | −4.2 |
| 5% w/v sodium chloride | −10.3 |
| 1% w/v propylene glycol | −0.8 |
| 5% w/v propylene glycol | −3.4 |

TABLE 2-continued

Effect of specific additives on the sol-gel transition temperature for a 24% w/v preparation of Polyoxypropylene-Polyoxyethylene Block Polymer (PBP) 407.

| Additive | Effect on transition temperature (° C.) |
| --- | --- |
| 1% w/v polyethylene glycol 400 | 0.0 |
| 5% w/v polyethylene glycol 400 | +0.2 |
| 1% w/v polyethylene glycol 2000 | +1.1 |
| 5% w/v polyethylene glycol 2000 | +2.8 |

In a preferred embodiment, the composition is applied to a surface of a microscope slide, a coverslip or a multichamber plate (e.g. a multiwell plate).

In a further preferred embodiment, the composition serves a support matrix for the analysis of particles involving light collection, including transmission, phase-contrast, fluorescence, fluorescence-lifetime, bioluminescence, chemo-luminescence, anisotropy, light scattering, and refractive index. For example, the composition may serve as a support matrix for the analysis of particles by imaging, microscopy or non-imaging plate based detection platforms.

Preferably, the particles are analysed by standard fluorescence microscopy.

More preferably, the particles are analysed by confocal laser scanning microscopy, multi-photon excitation laser scanning microscopy or fluorescence microscopy in which the image data collected are subjected to mathematical processing (including deconvolution) to provide depth-specific information.

Conveniently, the light originates the light originates from a genetically encoded construct in a cell to express a fluorescent molecule such as cells manipulated to express a fluorescent molecule, for example green fluorescent protein and/or spectral variants and/or stability variants thereof.

In a further preferred embodiment, the composition serves as a support matrix for the multi-dimensional analysis of particles, for example by 3D(x, y, z) imaging, time (kinetic) analysis and lamda (spectral) analysis.

Alternatively, the composition may serve as a support matrix for the kinetic analysis of particles.

In a particularly preferred embodiment of the first aspect of the invention, analysis of the particles is performed by high throughput screening.

In another preferred embodiment, the support matrix is for use in calibration, optical alignment or orientation in methodologies requiring the collection of light. For example, the analysis may be for calibration purposes, point-spread function determination and event orientation within optical slices of two or more dimensions.

In an alternative preferred embodiment, the composition serves as a particle mountant.

In a further preferred embodiment, the composition provides a means of controlling and/or modifying access of reactants and reporter molecules to particles.

Preferably, the composition further comprises fluorescent beads. For example, beads may be deposited on a surface or layer within said composition.

Advantageously, the composition comprises fluorescent beads of different sizes and/or different colours (such beads are available commercially from Molecular Probes [Invitrogen Corporation], Carlsbad, US).

Alternatively, or in addition, the composition further comprises a dye, such as a DNA fluorochrome. Suitable dyes are available commercially (for example, from Molecular Probes [Invitrogen Corporation], Carlsbad, US). Preferably, the dye exhibits cell permeant properties with excitation and emission wavelengths in the visible range spectrum, including the near infrared. Example of suitable dyes include calcein, propidium iodide and the SYTO series of dyes.

Most preferably, the composition comprises 1,5-bis{[2-(methylamino)ethyl]amino}-4,8-dihydroxy anthracene-9,10-dione (DRAQ5™; available from BioStatus Limited, Shepshed, UK) or a derivative thereof.

The composition may also further comprise one or more of the following additives:
1. a cell-fixing chemical, such as paraformaldehyde (PFA);
2. a chemo-attractant, i.e. a chemical agent, exogenously present, eliciting directional motility in a responsive cell;
3. an excipient for the purpose of cell protection or biological modification (such as a growth factor or signalling molecule); and/or
4. an excipient for the purpose of modifying the photophysical and/or photochemical effects of light illumination on cells or reporter molecules (for example, the excipient may reduce photobleaching of fluorescent reporter molecules or enhance photobleaching of extracellular fluorescent reporter molecules).

A second aspect of the invention provides a support matrix composition for the manipulation, processing or analysis of particles comprising a block polymer together with fluorescent beads and/or a dye.

Preferably, the composition exhibits the following properties:
1. gel-sol thermoreversibility;
2. micelle formation under gelling conditions;
3. optical compatibility;
4. controllable surfactant properties;
5. molecular sieving properties; and
6. biocompatibility.

Further preferred embodiments of the second aspect of the invention are as defined in relation to the first aspect of the invention.

For example, the particles may be any particles as defined above in relation to the first aspect of the invention, for example live, non-adherent cells.

Similarly, the block polymer may be any block polymer as defined above in relation to the first aspect of the invention, for example a block copolymer of polyoxyethylene and polyoxypropylene. Preferably, the block polymer (such as a block copolymer of polyoxyethylene and polyoxypropylene) may be present in the composition at a concentration of 24% (w/v).

Conveniently, the composition is applied to a surface of a microscope slide, a coverslip or a multichamber plate (for example, a 96-well, 384-well or 1536-well plate).

In a further preferred embodiment, the composition is suitable for the analysis of particles involving light collection, for example by imaging (e.g. 3D imaging), microscopy (e.g. fluorescence microscopy) or non-imaging plate based assays.

Preferably, the light being analysed is fluorescence, bioluminescence or chemoluminescence emissions. Most preferably, the composition is suitable for high throughput screening.

The composition according to the second aspect of the invention may be suitable for calibration, optical alignment or orientation in methodologies requiring the collection of light. For example, the composition may be used for calibration, point-spread function determination and event orientation within optical slices of two or more dimensions.

Alternatively, the composition may serve as a particle mountant and/or may provide a means of controlling access of reactants and reporter molecules to particles.

In a further preferred embodiment of the second aspect of the invention, the composition comprises fluorescent beads. For example, fluorescent beads may be deposited on surface within the composition. Preferably, the composition comprises fluorescent beads of different sizes and/or different colours (i.e. fluorescent spectral properties).

In an alternative preferred embodiment of the second aspect of the invention, the composition further comprises a dye, such as a DNA fluorochrome (for example, DRAQ5™ or a derivative thereof, available from Biostatus Limited, UK).

A third aspect of the invention provides a method of making a support matrix composition according to the second aspect of the invention comprising incorporating fluorescent beads and/or dye into a block polymer formulation. Preferably, the method comprises dissolving a block polymer in distilled water or phosphate-buffered saline, sterilising the solution formed thereby, and storing the solution at 4° C.

A fourth aspect of the invention provides a kit for making a support matrix composition according to the second aspect of the invention comprising a block polymer, fluorescent beads and/or a dye.

A fourth aspect of the invention provides a microscope slide, coverslip or multichamber plate comprising a support matrix composition as defined in any one of the preceding claims applied to a surface thereof. For example, the multichamber plate may be a 96-well, 384-well or 1536-well plate. Advantageously, the support matrix composition forms an addressable array for the purpose of mechanical delivery of analytes and subsequent optical analyses requiring the collection of light including transmission, phase-contrast, fluorescence, fluorescence-lifetime, bioluminescence, chemoluminescence, anisotropy, light scattering, and refractive index.

In a preferred embodiment of the fourth aspect of the invention, the support matrix composition is provided on the microscope slide, coverslip or multichamber plate in a dried form which requires rehydration prior to use.

A fifth aspect of the invention provides a method of making a microscope slide, coverslip or multichamber plate according to the fourth aspect of the invention comprising applying a support matrix composition as defined above in relation to the first or second aspects of the invention to a surface of the microscope slide, coverslip or multichamber plate.

Preferably, the method further comprises dehydrating the support matrix composition after it has been applied to the surface of the microscope slide, coverslip or multichamber plate.

A sixth aspect of the invention provides a kit for making a microscope slide, coverslip or multichamber plate according to a fifth aspect of the invention comprising a microscope slide, coverslip or multichamber plate and a support matrix composition as defined above in relation to the first or second aspects of the invention. Preferably, a multichamber plate comprising 96 wells, 384 wells or 1536 wells.

A seventh aspect of the invention provides a method of staining cells comprising covering or mixing cells to be stained with a support matrix composition according any to the second aspect of the invention. Preferably, the staining method permits live cells to be differentiated from dead (apoptotic) cells.

Additional aspects of the invention include
1. Use of polyoxypropylene-polyoxyethylene block polymer (PBP) at gelling concentrations (and at gelling temperatures) as an optically compatible means of trapping and immobilising particles for the purpose of calibration, optical alignment and/or orientation in methodologies requiring the collection of light (including fluorescence, fluorescence-lifetime, bioluminescence, chemiluminescence, anisotropy and light scattering).

2. The use of polyoxypropylene-polyoxyethylene block polymer (PBP) at gelling concentrations as an optically compatible means of trapping and immobilising live and/or fixed cells for the purpose of analysis in methodologies requiring the collection of light (including fluorescence, fluorescence-lifetime, bioluminescence, chemiluminescence, anisotropy and light scattering).

3. Use of a polyoxypropylene-polyoxyethylene block polymer (PBP) at gelling concentrations as an over-layering mountant for adherent cultures or planar preparations of live or fixed cells, for example to provide protection and/or a controlled environment by temperature change and gel concentration.

4. A method for the preparation of particles, beads or cells comprising centrifugation of the particles, beads or cells from an aqueous suspension into a polyoxypropylene-polyoxyethylene block polymer (PBP) gel phase within the same container.

5. A method for sequential live cell-lysed cell analysis in situ comprising immobilising live cells in polyoxypropylene-polyoxyethylene block polymer (PBP) at gelling concentrations and then diluting to impart surfactant properties to the PBP in order to lyse the cells.

6. A composition for in situ fixing, immobilisation/structure support and cell staining comprising polyoxypropylene-polyoxyethylene block polymer (PBP) at gelling concentrations and a cell fixing chemical and/or a dye.

7. Use of a polyoxypropylene-polyoxyethylene block polymer (PBP) at gelling concentrations for the preparation and immobilisation of encapsulated cells on porous or non-porous surfaces for the purpose of short term cultivation and or a sequential analysis in which the location of the sample is recognized for data linkage purposes.

8. Use of a polyoxypropylene-polyoxyethylene block polymer (PBP) at gelling concentrations for the preparation and immobilisation of encapsulated cells on porous or non-porous surfaces for the purpose of short-term cultivation and or a sequential analysis in which the location of the sample is recognized for data linkage purposes.

9. Use of a polyoxypropylene-polyoxyethylene block polymer (PBP) at gelling concentrations for the preparation of encapsulated cells or particles for the purposes of sample protection, manipulation or analysis.

10. Use of a polyoxypropylene-polyoxyethylene block polymer (PBP) at gelling concentrations for the controlled carrier and delivery of molecules to cells or particles by passive diffusion or electrophoresis for the purpose of a controlled analysis methodologies.

11. Use of a polyoxypropylene-polyoxyethylene block polymer (PBP) at gelling concentrations for the thermally controlled presentation of cells or particles to a surface.

12. A method of preparation of Polyoxypropylene-Polyoxyethylene Block Polymer (PBP) as defined above in which the gel form is prepared, deposited at known volumes and by mechanical means into the wells of multi-well plates and subsequently de-hydrated to provide for storage or transport. In a preferred embodiment the multi-well plates will comprise 96-well, 384-well, or 1536-well formats.

13. A method of preparation of Polyoxypropylene-Polyoxyethylene Block Polymer (PBP) as defined above in which the gel form is prepared, deposited at known volumes and by mechanical means onto a surface such as glass and subsequently de-hydrated to provide for storage or transport. In a preferred embodiment the pattern of PBP deposits would form an addressable array for the purpose of mechanical delivery of analytes and subsequent optical analyses requiring the collection of light including transmission, phase-contrast, fluorescence, fluorescence-lifetime, bioluminescence, chemoluminescence, anisotropy, light scattering, and refractive index.

14. A method of preparation of Polyoxypropylene-Polyoxyethylene Block Polymer (PBP) as defined above in which the gel form is prepared as in claim 20 and subsequently re-hydrated by the introduction of appropriate volumes water or aqueous solutions of user-specified solutes. In a preferred embodiment the multiwell plates will comprise 96-well, 384-well, or 1536-well formats.

15. A method of preparation of Polyoxypropylene-Polyoxyethylene Block Polymer (PBP) as defined above in which the gel form is prepared as in claim 20 and subsequently re-hydrated by the introduction of appropriate volumes of aqueous suspensions of particles or live cells or fixed cells for the purpose of optical analyses requiring the collection of light including transmission, phase-contrast, fluorescence, fluorescence-lifetime, bioluminescence, chemoluminescence, anisotropy, light scattering, and refractive index. In a preferred embodiment the multiwell plates will comprise 96-well, 384-well, or 1536-well formats.

16. Method of sample preparation using Polyoxypropylene-Polyoxyethylene Block Polymer (PBP) as defined above for the purpose of controlled re-hydration of particles or live cells or fixed cells in with the process of re-hydration results in a stratification of the particles or live cells or fixed cells aiding the process of optical analysis by increasing their frequency within a given optical plane Properties and General Claims for PBP in Thermoreversible Gels for Cell and Particle/Bead Preparation, Manipulation, Processing and Analysis Using Fluorescence-Based Technologies The current claims arise from the unique combinations of block polymer properties for novel applications. These properties are thermoreversible gel-sol formation where sol formation is favoured at low temperatures, particle/cell immobilisation, low toxicity, optical compatibility, molecular sieving and surfactant. The rapid formation of a gel at the transition temperature reduces the surfactant properties of aqueous PBP providing an immobilising and support matrix for the manipulation, analysis or processing of live cells. In a preferred embodiment research, diagnostic and screening assays using biological samples which need to be immobilised during continuous or periodic analyses by microscopy or imaging methods thereby reducing the compromising effects of: cell motility, cell detachment from a substrate, the effects of Brownian motion, physical disturbance of cell locations or the loss of inter-relationships during sample manipulation. Live cell compatible immobilisation methodologies are vital for the sequential imaging of different optical planes for 3D re-construction or acquisition of images with time for kinetic analyses using laser scanning and camera-based microscopy approaches. PBP gel properties can be modified by formulation providing block polymers with different transition temperatures suitable for different applications.

Protocol Overview and General Considerations

The invention relates to the use of a cell- or particle- or reagent-support/embedding matrix based upon aqueous formulations of a thermo-reversible gel comprising in a preferred embodiment Polyoxypropylene-Polyoxyethylene Block Polymer (PBP) providing advantageous properties for manipulation, processing and analysis. The following protocols describe typical methods for the preparation of thermor-eversible gels exemplified with Pluronic® F-127. F-127 (F-127 polyol manufactured by BASF Corp., NJ) powder can be dissolved in 1× buffer (e.g. exemplified here using phosphate buffered saline) in deionised water at around 1-4° C. The low temperature of 4° C. is necessary because both block copolymers can be readily dissolved in aqueous media at that temperature. This results in a homogenous solution, mainly consisting of unimeric molecules. For example a 21.2% (w/v) solution of F-127 in 1× buffer has a low viscosity at temperatures approximately 4° C., at which the fluid can be manipulated for example by pressure, centrifugation etc. In this fluid form cells or particles can be introduced at low temperature preserving cell function or particle integrity without the thermal shock potential of using gels which only become liquid at elevated temperatures (>37° C.). In the fluid form cell and particle mixing can be achieved simply. In the fluid form other excipients, such as dyes (fluorescent probes) and reporter molecules, can be introduced to generate homogeneous preparations. Recovery of cells or particles from the liquid phase, or from dilutions of the gel in chilled buffers, can be achieved by conventional methods including centrifugation methods, filtration or magnetic separation.

At room temperature (above 15° C. selected by formulation to achieve a gel form at room temperature to 37° C.), the middle P block of F-127 copolymer becomes hydrophobic. The viscosity suddenly increases and the system becomes gel-like and provides an immobilising phase. Pluronic® F-127 in a low concentration (non-gelling) solution has both non-ionic detergent properties and dispersive properties ("Intracellular ion activities and membrane transport in parietal cells measured with fluorescent dyes." Negulescu P A, Machen T E. *Methods Enzymol* 192, 38-81 (1990)) which may not always be acceptable for cell handling, especially in studies in which detergent-lipid interactions may influence cellular membrane parameters.

The PBP gel form can act as a support matrix to immobilise cells or particles for example to reduce movement for the purposes of imaging. Immobilisation is important to allow for the inspection of high density and information-rich fields (e.g. counting of cell/particle subsets marked by different fluorescent dyes or features), the imaging of changes in cell/particle features with time, the multiplex analysis of cells/particles that require sequential acquisition, the imaging of asynchronous events in fields of cells/particles, and the high resolution imaging of sub-cellular events which could be compromised if the cell itself was mobile. Gel formation also reduces the delivery rate of dye molecules, for example to embedded cells, and therefore provides an element of control which can be exploited to enhance or extend the form or dynamic range of an assay (e.g. separating fast and slow staining populations with a convenient analysis timescale within a diffusion-limited system) and to permit the manipulation of dye preparations in higher viscosity and hence safer formulations (e.g. reducing the rate of aerosol formation or of transdermal delivery in laboratory accidents).

FIG. 1 shows a typical PBP viscosity-temperature profile indicating the parameters and the range of values that are pertinent to the utilisation of a thermo-reversible formulation for cell/particle manipulation and dye delivery. The sol-gel transition temperature (t50%) is a measure of the temperature at which to half the maximum gel viscosity is attained. The values t25% and t75% refer to the temperature at 25 and 75% of the maximum viscosity respectively. In addition to the measurement of these values, the pH of the formulation (e.g. as adjusted to pH 7.2-7.4 through the use of phosphate buffered saline as the buffer) is important for cell viability.

The handling concept behind the gel is that it would be stored routinely in the cold (providing a liquid reagent form). The liquid form is manipulated cold but forms a gel within seconds as the temperature is increased. Controlling the warming process will provide for different micellar qualities in terms of the degree of ordering. The rapidity permits incorporation into rapid assays. The instantaneous conversion from sol-to-gel phase provides a route for incorporation into assays. The liquid form can be used to trap, support, overlayer, or suspend particles, beads, cells etc prior to or during manipulation (e.g. resuspend a cell pellet). Upon temperature shift (e.g. positive or passive warming) the gel stiffens providing a cell/particle mountant.

General methodologies can be described which provide for applications in which live or fixed cells, particles or beads can be incorporated into the gel with formulations which may include informative dyes or other reporter molecules. These basic protocols can be adapted for specific applications in candidate product screening in drug discovery, cell- and particle/bead-based biotechnologies and numerous applications in imaging and microscopy and non-imaging plate based assays.

EXAMPLES

Example I

Methodological Aspects

Figure 1:
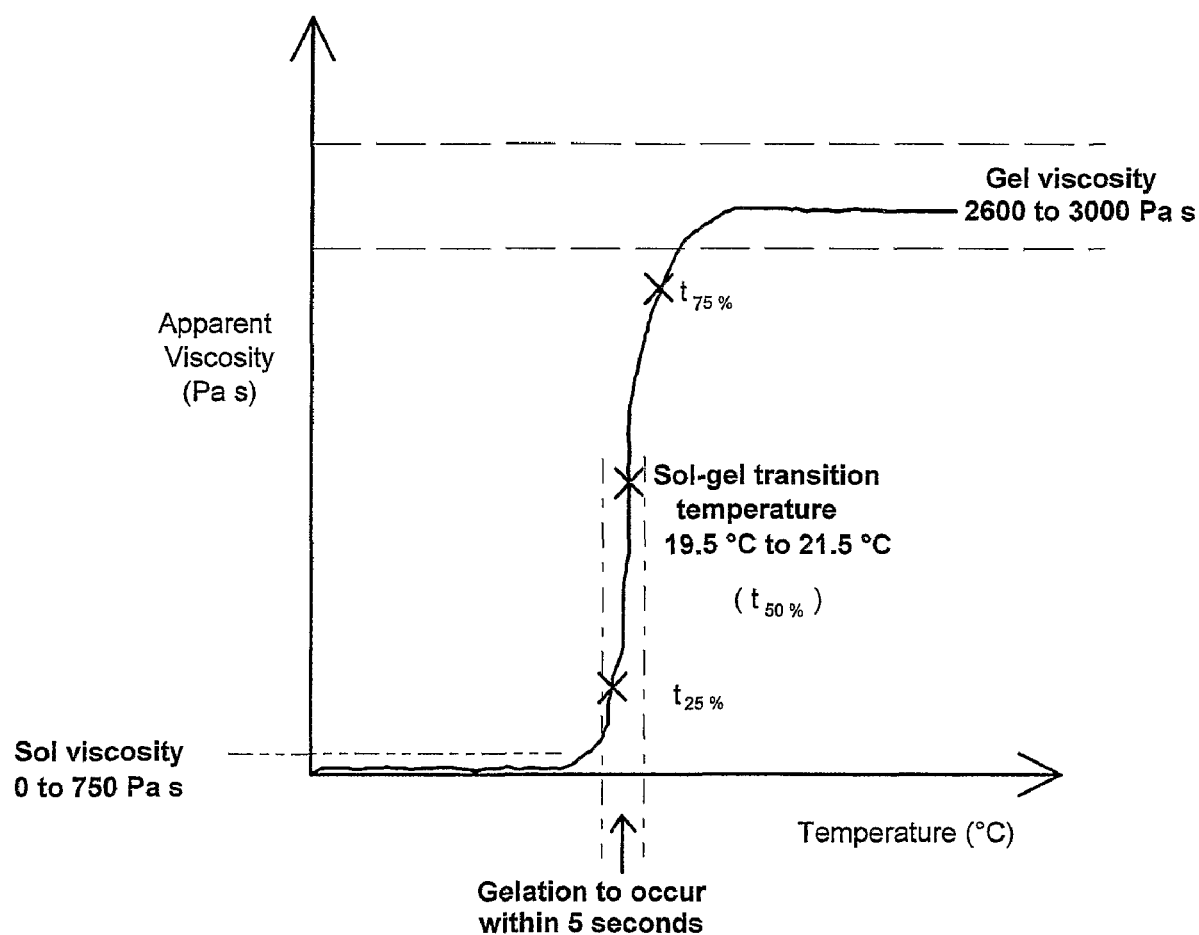
FIG. 1 shows a typical PBP viscosity-temperature profile indicating the parameters and the range of values that are pertinent to the utilisation of a thermo-reversible formulation for cell/particle manipulation and dye delivery.

A Typical Protocol for the Preparation of Aqueous Sterile PF-127 Poloxamer Solutions
i) Aqueous poloxamer solutions were prepared on a percentage weight in volume basis, by the cold process similar to that described by Schmolka in 1972 (Schmolka, I. R. (1972) Artificial skin I. Preparation and properties of Pluronic® F-127 gels for treatment of burns. *J. Biomed. Mater. Res.* 6, 571-582.). PBP is added slowly to distilled water and stirred constantly. The sol is thoroughly mixed and stored at 4° C. until required.
ii) PF-127 (e.g. batch number WPDL-510B) was obtained from BASF Corporation (Preston, Lancashire, UK). PF-127 solutions used in cell mountant protocols are prepared using, for example, phosphate buffered saline (PBS). Different formulations of PBS can be used. Typical formulations for Phosphate-Buffered Saline are:
a. PBS as a 1× liquid, pH: 7.4±0.05 (Potassium Phosphate monobasic ($KH_2PO_4$) 1.06 mM, Sodium Chloride (NaCl) 155.17 mM, Sodium Phosphate dibasic ($Na_2HPO_4$-$7H_2O$) 2.97 mM)
b. Dulbecco's Phosphate-Buffered Saline (D-PBS) (1×) liquid containing calcium and magnesium (Calcium. Chloride ($CaCl_2$) (anhyd.) 0.901 mM, Magnesium Chloride ($MgCl_2$-$6H_2O$) 0.493 mM, Potassium Chloride (KCl) 2.67 mM, Potassium Phosphate monobasic ($KH_2PO_4$) 1.47 mM, Sodium Chloride (NaCl) 137.93 mM, Sodium Phosphate dibasic ($Na_2HPO_4$-$7H_2O$) 8.06 mM). [REFERENCE: Dulbecco, R. and Vogt, M., (1954) Plaque formation and isolation of pure lines with Poliomyelitis viruses. *J. Exp. Med.*, 98:167].
iii) PF-127 solutions requiring steam sterilisation are transferred to 100 mL glass bottles, autoclaved at 120° C. for 20 minutes (USP, XX11NFXV11) and subsequently stored at 4° C. until required. Solid PF-127 requiring dissolution in D-PBS or a buffer of choice such as RPMI culture medium (either alone, fully supplemented or supplemented with glutamine and antibiotics) is weighed under aseptic conditions and added to the sterile medium without mixing and stored at 4° C. for 12 hours. After this period, any clumps of PF-127 remaining are dispersed under aseptic conditions using a sterile spatula and the mixture stored for a further 24 hours at 4° C. until PF-127 hydration was complete as judged by the presence of a transparent solution (as defined by reference to refractive index).
iv) The presence of heat labile components in the buffer used in any cell culture experiments may prevent steam sterilisation of PF-127 hydrated in such media. Instead, immediately prior to use the PF-127 solutions can be filter sterilised (0.2 μm pore size filters). This approach also permits the preparation of thermolabile excipients, a procedure not possible with dissolution in gels requiring heating to achieve liquid form.
v) Over-strength PF-127 solutions are used to dissolve excipients, for example drug stock solutions, such that upon mixing the required concentration of a dye (e.g. 20 μM DRAQ5™ or 1 μg/mL propidium iodide) and PF-127 gel was obtained.

B Typical Step-Wise Protocol for the Physical Handling of PBP Gel (Exemplified Here as a 24% w/v Preparation of PF-127 in PBS) for its Use as a Cell/Particle Mountant
i) Cell preparations are made by a standard cell culture method of choice, including: using attached cells growing on a microscope slide surface (e.g. a chamber slide or multichamber plate) or on a coverslip (e.g. coverslip culture), or deposited upon a microscope slide (e.g. by smear formation or droplet delivery or cyto-centrifugation).
ii) The PBP gel is prepared in a convenient container. Here a dropper-bottle preparation is described for cells physically mixed into the PBP gel or for cells deposited on the surface of a microscope slide or growing on a coverslip).
iii) Remove the PBP gel dropper bottle from the 4° C. refrigerator (store upright overnight at 4° C. prior to use, and try not to introduce bubbles into the liquid form when using the dropper) and place it on crushed ice to maintain the PBP gel as liquid form and to further chill the glass dropper inside the bottle.
iv) Take a glass microscope slide (room temperature), place it on a flat surface and quickly use the dropper to deposit one drop of PBP gel into the centre of the slide. Return the dropper to the chilled bottle immediately. The gel will rapidly stiffen on the surface of the microscope slide. Do not touch.
v) Take a standard coverslip (room temp) and gently/evenly place it on top of the central mound of gel without pressing or trapping air at the point of contact. The coverslip will appear as a "hat" balancing on the gel.
vi) Place the microscope slide on a bed of ice (or preferably onto a flat metal plate on a bed of ice or a Peltier device to provide a convenient chilling surface).
vii) Watch the gel carefully and within seconds the gel will undergo reverse transition and become a liquid, spreading as a mountant under the coverslip.

viii) When gel spreading has occurred, remove the slide from the chilling plate and place the underside of the slide in contact with a warming surface, for example a palm of the hand. The gel will stiffen quickly, and retain the coverslip in place even at room temperature. The slide can be inverted without movement of the coverslip. The gel can be removed from the surface by irrigation using chilled water or buffer.

ix) With practice the deposition of the correct amount of PBP gel onto the slide, the application of the coverslip and the sequence of temperature shifts can produce a mounted sample in 30 secs with perfect filling of the coverslip and no trapped bubbles.

x) The preparation is then analysed by standard microscopy methods.

C Typical Protocol for the In Situ Staining of Live Cells at Room Temperature Using an Aqueous Sterile PF-127 Poloxamer Solution Prepared in Phosphate Buffered Saline at 24% w/v for the Purpose of Staining Nuclear DNA i) An over strength aqueous poloxamer solution were prepared on a percentage weight in volume basis as described and mixed with a concentrated stock solution of the DNA dye DRAQ5™ to yield a final concentration of 20 µM DRAQ5™ in 24% PF-127.

ii) Using an ice-chilled pipette a 4° C. solution of DRAQ5™/PF-127 is over layered quickly onto a cell monolayer culture (e.g. human osteosarcoma cell line U2-OS growing in a chamber slide), obtained using standard cell culture methods. Prior to over layering the gel the culture medium is removed and the monolayer washed using chilled phosphate buffered saline and the chamber slide placed on a chilled surface.

iii) A coverslip is then placed onto the over layered gel and the mounting procedure completed as described above.

iv) The preparation is then analysed by standard fluorescence microscopy methods to examine nuclear morphology of the cells as they in situ stain with the DRAQ5™/PF-127 preparation.

D Typical Protocol for the In Situ Staining of Live Cells at Room Temperature Using an Aqueous Sterile PBP Solution Prepared in PBS at 24% w/v for the Purpose of Distinguishing Live and Dead (Apoptotic Cells) Using Differential Staining by Propidium Iodide i) An over strength aqueous PBP solution was prepared on a percentage weight in volume basis as described and mixed with a concentrated stock solution of the viability dye propidium iodide to yield a final concentration of 1 µg/mL in propidium iodide in 24% PF-127).

ii) Using an ice-chilled pipette a 4° C. solution of PI/PBP solution is mixed with a high-density suspension of cells for analysis (e.g. human B cell lymphoma cell line growing as a suspension culture), obtained using standard cell culture methods. The chilled, mixed sample is pipetted onto a chilled microscope slide and a coverslip added as described above.

iii) The preparation is then analysed by standard fluorescence microscopy methods to examine the presence of rapidly stained cells showing abnormal nuclear morphology (apoptotic or necrotic) or cells resisting staining representing those with intact plasma membranes. Here trapping in the cell permits the kinetics of staining to be observed and permits repeated analysis of a field of immobilised cells, which would normally be lost in an image/microscopy, based assay.

iv) Cell samples may be pre-stained with propidium iodide in aqueous suspensions prior to transfer to an aqueous PBP solution for example the transfer of samples initially prepared for flow cytometry and subsequently analysed by imaging in gel.

E Typical Protocol for the Preparation of Fluorescent Cells (e.g. Expressing Green Fluorescent Protein) in PBP Gel for Live Cell Imagine i) Cells carrying a fluorescent reporter are prepared using standard cell culture methods either as attached cultures or resuspended cells at high density in a medium of choice.

ii) For attached cell cultures, PBP gel in liquid phase is over-layered as described above.

iii) For cell suspensions, aliquots are mixed directly into the PBP gel in liquid phase and pipetted directly onto a microscope slide with a coverslip added as described above.

iv) The live cell preparations are then analysed by standard fluorescence microscopy methods to examine features of interest.

Additional applications of the invention include the following:

Polyoxypropylene-Polyoxyethylene Block Polymer (PBP) at gelling concentrations can be used to act as an optically compatible means of trapping and immobilising particles for the purpose of calibration, optical alignment and orientation in methodologies requiring the collection of light including fluorescence of bioluminescence emissions. In a preferred embodiment fluorescent beads deposited on a surface within a PBP gel would be used in fluorescence microscopy systems (e.g. confocal laser scanning microscopy system or multi-photon excitation laser scanning microscopy) to provide a means of calibration, point-spread function determination and event orientation within optical slices two or more dimensions.

Calibration samples include the co-mixing of beads with cells within the PBP gel to provide a depth versus fluorescence correction versus scattering for the determination of point spread function in the same live sample conditions. Such samples may also be used to provide an indication of performance of optical elements or instrument set-up. Such a method would be appropriate for any type of multi-dimension imaging which requires calibration of x, y or z-axis resolution. Calibration is required in order to measure and consequently correct for sample derived aberrations. Embedded beads co-mixed with the cellular sample are therefore appropriate for multi-dimensional resolution measurement particularly x,y,z axis resolution, including the point spread function obtained from sub-resolution beads. Other aberrations require depth dependent correction of fluorescence, fluorescence spectral overlap and cross talk measurement.

Polyoxypropylene-Polyoxyethylene Block Polymer (PBP) at gelling concentrations can be used to act as an optically compatible means of trapping and immobilising live and fixed cells for the purpose of analysis in methodologies requiring the collection of light including fluorescence or bioluminescence emissions. The cells may be non-adherent or processed cell suspensions. In a preferred embodiment the fluorescence would originate from a fluorescent molecule manipulated to be expressed by the cell such a green fluorescent protein (GFP).

Polyoxypropylene-Polyoxyethylene Block Polymer (PBP) at gelling concentrations as an over-layering mountant for adherent cultures or planar preparations of live or fixed cells providing a convenient mountant for protection of cells and in situ staining or labelling of cells. Here the sol-gel transition as a function of temperature provides a novel means of spreading the mountant at lower temperature and controlling the gel depth by halting spreading through gel formation by raising local temperature of the preparation. The adherent properties would allow for inversion of a mounted specimen so that inverted microscopy formats can be used. Here the gel provides an aqueous-gel phase between the specimen and another optical interface for imaging. In a preferred embodiment the fluorescence would originate from a fluorescent molecule manipulated to be expressed by the cell such a green fluorescent protein (GFP).

Polyoxypropylene-Polyoxyethylene Block Polymer (PBP) at gelling concentrations can be used in a method of preparation of particles, beads or cells ('analytes') by the centrifugation from aqueous suspension into a PBP gel phase within the same container. In a preferred embodiment the PBP gel is present below an over-layering aqueous phase comprising a suspension of said analytes and maintains a gel-aqueous interface by temperature control. Centrifugation forces entry of analytes into the gel. Analytes deposited into the gel phase can be recovered by temperature-controlled transition to a sol following removal the aqueous over layer.

Analytes can be pre-labelled with fluorescent or bioluminescent probes. Additionally analytes which are fluorescent or bioluminescent molecular probes may be present either in the aqueous phase or in the gel phase to enable an optical analysis of the suspended particles, beads or cells. In a preferred embodiment the fluorescent molecular probe is the anthraquinone DRAQ5™.

Polyoxypropylene-Polyoxyethylene Block Polymer (PBP) at low non-gelling concentrations has surfactant properties which can provide cell disrupting or lytic properties for the release of molecules for primary and/or secondary analyses. Modulation of properties would require a shift in concentration of PBP by in situ dilution and or a shift in temperature. In a preferred embodiment PBP gels solubilised in situ would impart surfactant properties and provide for a sequential live cell-lysed cell analysis methodology.

Polyoxypropylene-Polyoxyethylene Block Polymer (PBP) at gelling concentrations can be combined with cell fixing chemicals (e.g. paraformaldehyde) and or dyes (e.g. a DNA fluorochrome) to provide unique multi-functional agents for in situ fixing, immobilisation/structure support and cell staining. In a preferred embodiment such multi-function agents would reduce processing time, minimise cell loss through a reduction in the number of processing steps (e.g. in fixation schedule that require washing and fluid removal steps) and provide a means for maintaining osmotic environments, metabolic gradients and structural/mechanical integrity.

The formation of Polyoxypropylene-Polyoxyethylene Block Polymer (PBP) gels to enable the preparation and immobilisation of encapsulated prokaryotic cells on porous or non-porous surfaces for the purpose of short term cultivation and or a sequential analysis in which the location of the sample is recognised for data linkage purposes. In a preferred embodiment temperature-shifting the low temperature liquid phase encapsulation of a prokaryotic cell(s) could be used to trap cells at a specific location at which a drug can be delivered for the purpose of chemosensitivity testing.

The formation of Polyoxypropylene-Polyoxyethylene Block Polymer (PBP) gels to enable the preparation and immobilisation of encapsulated eukaryotic cells on porous or non-porous surfaces for the purpose of short term cultivation and or a sequential analysis in which the location of the sample is recognised for data linkage purposes. In a preferred embodiment temperature-shifting the low temperature liquid phase encapsulation of a eukaryotic cell(s) is used to trap cells at a specific location at which a subsequent analysis of a gene sequence(s) and or protein(s) or other cell-originating molecules.

The formation of Polyoxypropylene-Polyoxyethylene Block Polymer (PBP) gels to enable the preparation and immobilisation of encapsulated cells on porous or non-porous surfaces for the purpose of short term cultivation and or a sequential analysis in which the location of the sample is recognised for data linkage purposes. In a preferred embodiment temperature-shifting the low temperature liquid phase encapsulation of a eukaryotic cell(s) is used to trap cells at specific locations for the purpose of detecting and analysing the presence or absence of parasites including the intracellular forms of *Plasmodium* species in the diagnosis of malaria and for the purpose of species and variant identification.

The formation of Polyoxypropylene-Polyoxyethylene Block Polymer (PBP) gels to enable the preparation of encapsulated cells or particles for the purposes of sample protection, manipulation or analysis. In a preferred embodiment the low temperature liquid phase encapsulation of a cell or particle permits the generation of droplets for the purpose of preparing arrays or replicates through the delivery of such droplets to a receiving surface or container prior to or following analysis of informative features of the encapsulated sample.

A methodology to provide a means of the pre-building of modular assay systems/devices for sequential processing regulated by the properties of the thermoreversible gels. In passing through the transition temperature, for example at the point of droplet formation or delivery, encapsulated samples would suffer reduced evaporation stress for live cell preparations but have increased surface adhesion properties. In a preferred embodiment encapsulated cells offer a physical protection for cells from mechanical stress imparted by sorting and arraying instrumentation.

The rapid formation of the Polyoxypropylene-Polyoxyethylene Block Polymer (PBP) gel provides initially an immobilising layer on the cells. With the addition of potential chemo-attractants within the gel or in a layer above the gel, this gradient becomes an active layer for stimulating cells or attracting/sorting cells away from unstimulated counterparts. The thermoreversibility allows these cells to be selectively removed and further processed.

The micelle environment of the Polyoxypropylene-Polyoxyethylene Block Polymer (PBP) provides for the controlled carrier and delivery of molecules (e.g. reactants, reporter fluorochromes or conjugates thereof) to cells or particles by passive diffusion or electrophoresis for the purpose of a controlled analysis methodologies. In a preferred embodiment the molecular sieve effects of the PBP gel would effect a sequential delivery of reactants and fluorescent or bioluminescent reporter molecules within sample preparations.

The addition of excipients for the purpose of cell protection or biological modification would impart additional functionalities to Polyoxypropylene-Polyoxyethylene Block Polymer (PBP) gels. For example, the inclusion of growth factors or signalling molecules to maintain or modify specific cellular phenotypes.

The addition of excipients for the purpose of modifying the photophysical and photochemical effects of light illumination on cells or reporter molecules would impart additional functionalities to Polyoxypropylene-Polyoxyethylene Block Polymer (PBP) gels. For example, excipients may be included to reduce the photobleaching of fluorescent reporter molecules.

The formation of Polyoxypropylene-Polyoxyethylene Block Polymer (PBP) gels to enable the thermally controlled presentation of cells or particles to surfaces, which enhance or enable assay performance. In a preferred embodiment the assay would exploit surface plasmon resonance effects or light collection from highly restricted depths at optical interfaces.

The block copolymer relevant to this invention may comprise polyoxyethylene and polyoxypropylene. Accordingly, gel-forming preparations include those described as Pluronics® F127, F108, F98, F87 and F88 (Pluronic® is a registered trademark of BASF Corporation).

Example II

Use of Block Polymer Compositions of the Invention in the Analysis of Fluorescent or Dyed Cells 1. General Methods for the Preparation of a Cell Line Expressing EGFP and its Optical Analysis Preparation of construct. The cell cycle phase marker DNA construct (GE Healthcare; Cardiff UK) was prepared from three DNA fragments that were fused in frame and cloned into a pCI-Neo (Promega) vector that had been cut with BglII and NheI to remove the CMV promoter. The three fragments used were the cyclinB1 promoter, the N-terminal 171 amino acids of the human cyclin B1 coding region and EGFP. The cyclin B1 promoter was amplified from a construct described previously22 using PCR and the primers 5'-CGCGGCAGCT-GCCCGAGAGCGCAGGCGC-3' and 5'-CGCAAGCTTC-CTCTTCACCAGGCAGCAGCTC-3'. The N-terminal region of cyclin B1 mRNA, encoding the cyclin B1 destruction box and the CRS but excluding the CDK binding site was amplified with HindIII and BamHI ends using PCR and the primers 5'-GGGAAGCTTAGGATGGCGCTCCGAGT-CACCAGGAAC-3' [SEQ ID NO:1] and 5'-GCCGGATC-CCACATATTCACTACAAAGGTT-3' [SEQ ID NO:2] from a cyclinB1 cDNA described previously5. The gene for EGFP was amplified from pEGFP-N2 (Clontech) with primers 5'GGTACGGGCCGCCACCATGGGATC-CAAGGGCGAGGAGCTGTTCAC [SEQ ID NO:3] and 5'-GGTACGGGTTAACCGGTCTTGTA-CAGCTCGTCCATG 3' [SEQ ID NO:4].

All three fragments were fused and the integrity of the final clone confirmed by sequence analysis.

Cell reporter system. The parental cell line used in these studies was a human osteosarcoma cell line derived from a 15 year old Caucasian female U-2 OS (American Type Culture Collection [ATCC] HTB-96). U-2 OS cells was transfected with the cell cycle marker DNA construct using Fugene (Roche) according to the manufacturers instructions. Following selection with 1000 µg/ml Geneticin (Sigma G7040) the expressing cells were enriched using high-speed fluorescence activated cell sorting (MoFlow; DAKO-Cytomation) and sorted into 96 well plates (1 green fluorescent cell/well). Colonies were expanded and clones whose green fluorescence varied with the cell cycle as predicted for a cyclin-based reporter, as determined by conventional flow cytometry, were expanded and a high expressing subline maintained.

Growing and maintenance condition. The stably transfected cells were maintained at 37° C. and 5% CO2 using standard tissue culture techniques. Media used was McCoys 5A modified (Sigma) supplemented with 2 mM glutamine, 100 units/ml penicillin, 100 mg/ml streptomycin, 10% fetal calf serum and 1000 µg/ml geneticin.

Time-lapse/camera imaging. High resolution fluorescence cell tracking was performed with cells seeded into 8 well Nunc coverglass chambers (Labtek Inc). Culture dishes were placed on to a time-lapse instrument designed to capture bright-field phase images and GFP fluorescence (480/25 nm excitation and 525/30 nm emission). An Axiovert 100 microscope (Carl Zeiss, Welwyn Garden City, UK), was fitted with an incubator for 370 C/5% CO2 maintenance (Solent Scientific, Portsmouth, UK), and an ORCA-ER 12-bit, CCD camera (Hamamatsu, Reading, UK). Illumination was controlled by means of a shutter in front of the transmission lamp, and an x, y positioning stage with separate z-focus (Prior Scientific, Cambridge, UK) controlled multi-field acquisition. Image capture was controlled by AQM 2000 (Kinetic Imaging Ltd). All images were collected with a 40×, 0.75 NA air apochromat objective lens providing a field size of 125×125 mm. Sequences were captured as required. When required analysis of the images was performed with the integrated AQM 2000 software package (Kinetic Imaging Ltd). Each cell in the field was tracked individually. Fluorescence tracking on a single cell basis was achieved in Lucida (KI Ltd). Fluorescence was recorded in a region of interest.

2. Typical Analysis of Fluorescent Cells in Gel.

Figure 2:
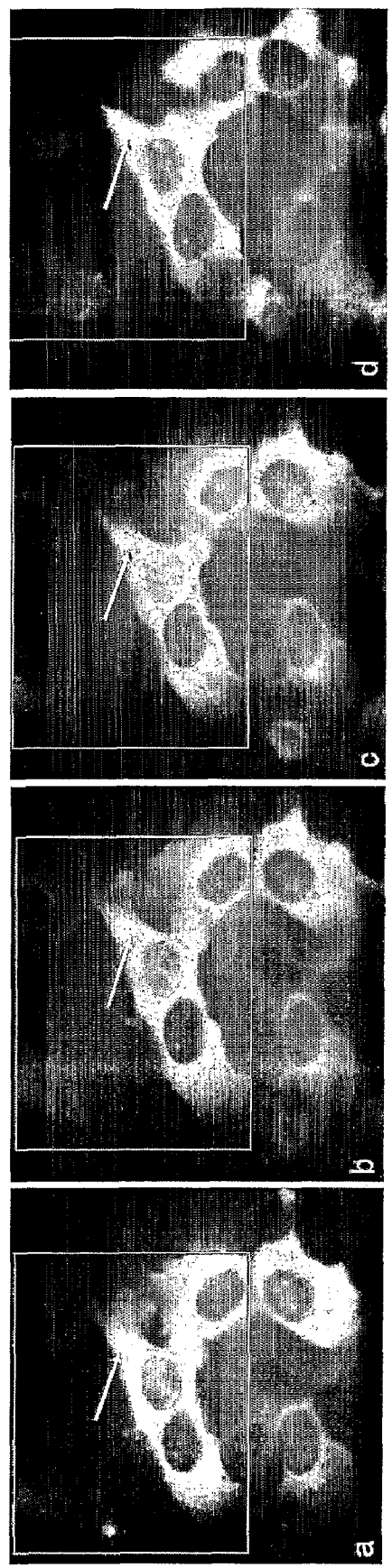
FIG. 2 shows camera images of EGFP-associated fluorescence in U2-OS human tumour cells held in gel, demonstrating the maintenance of cellular integrity and EGFP expression in the cytoplasm (arrow). (Panels: a, cell in full culture medium; b-d, cells overlayered with gel and imaged at 0 [b], 10 [c] and 60 [d] min at 37° C.

FIG. 2 shows typical results for EGFP-associated fluorescence in expressing cells imaged in culture medium (panel a), in which the marked region shows the presence of a group of 3 cells expressing high levels of EGFP in the cytoplasm (arrow). Following capture of the image cells, culture medium was aspirated and the cell monolayer overlayered with a chilled (4° C.) 24% w/v gel (PF-127; in sol form) prepared in PBS, returned to the imaging platform (at 37° C.; the overlayer forming a supporting gel at this temperature) and the location of the field re-found. Further fluorescence images were captured of the same cells at 0, 10 and 60 min incubation in gel. The images clearly show the maintenance of cellular integrity (flattened cells) and GFP expression in the cytoplasm.

3. Typical Analyses of More than One Fluor in Live Cells in Gel: EGFP-Expressing Cells in Gel (24% w/v PF-127 Prepared in PBS) Co-Stained with a DNA Dye (DRAQ5).

Figure 3:
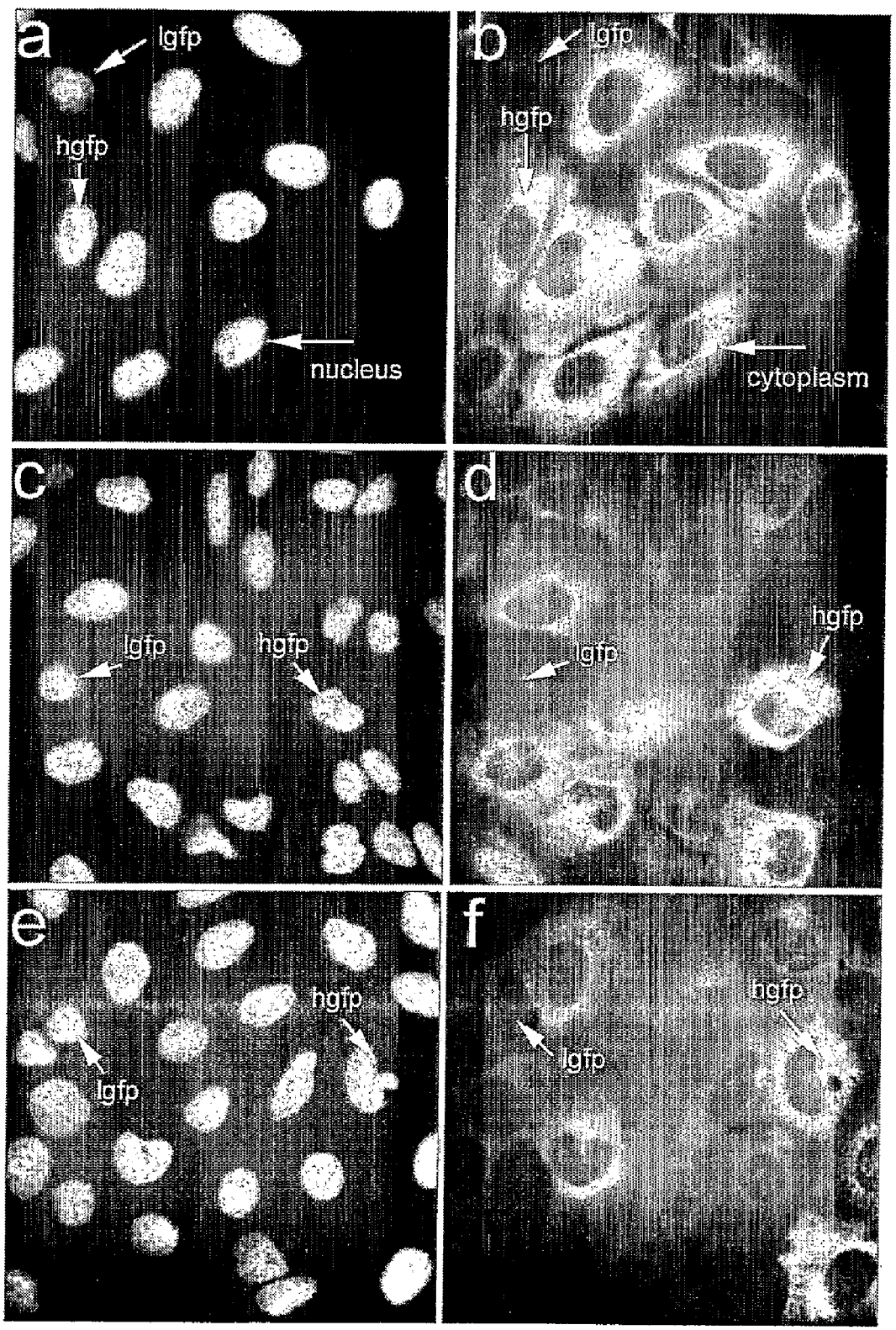
FIG. 3 shows camera images of EGFP expressing U2-OS human tumour cells. mounted in gel following exposure to the nuclear locating fluorescent dye DRAQ5 (a: b)

FIG. 3 shows typical results for EGFP-associated fluorescence in 3 samples stained for nuclear DNA using the fluorescent agent DRAQ5. Paired images show DRAQ5-associated far-red fluorescence (FIG. 3 left panels a, c and e) or EGFP green fluorescence (FIG. 3 right panels b, d and f). Panels a and b show results for the same cells stained in PBS with DRAQ5 (20 µM×10 min) and imaged in PBS permitting the identification of cells (presence of a nucleus; arrowed) with high-(hgfp) or low-(lgfp) EGFP expression within the cytoplasm (arrowed). Panels c and d show cells also pre-stained using DRAQ5 in PBS but overlayered with gel (see above) after aspiration of the DRAQ5 solution. The images in panels c and d show the continued ability to distinguish hgfp and lgfp expressing cells. Panels e and f show cells stained with DRAQ5 in the gel overlayer for 1 h (DRAQ5 20 µM in 24% w/v PF-127 prepared in PBS; at 37° C.), demonstrating the ability to distinguish hgfp and lgfp cells using an in-gel staining methodology. The images clearly show the maintenance of cellular integrity (flattened cells) and GFP expression in the cytoplasm.

4. Typical Light Transmission and Fluorescence Analysis of Cells Stained in Gel Using a Cell Permeant Dye (DRAQ5).

Figure 4:
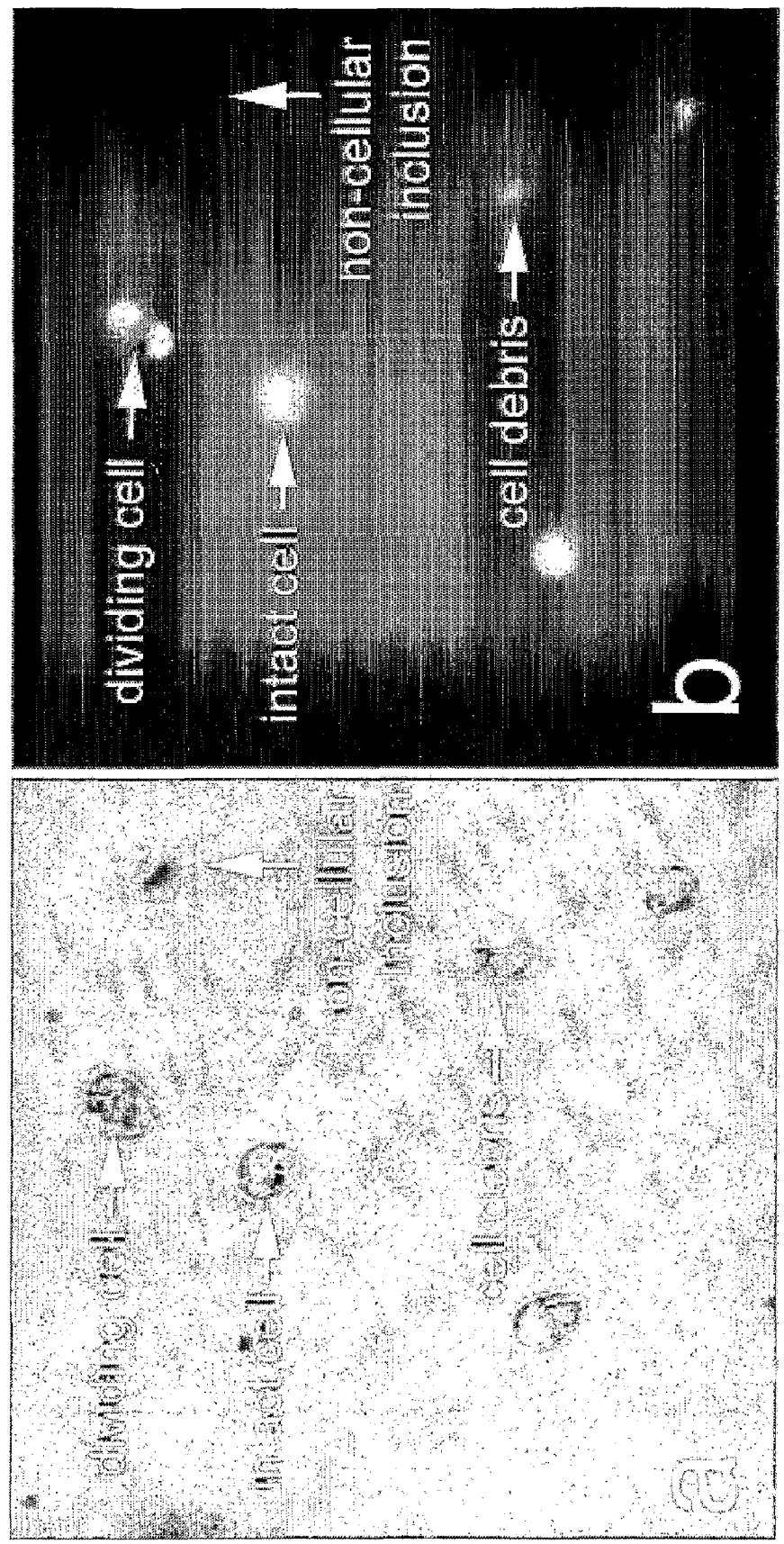
FIG. 4 shows camera images of DRAQ5 in gel stained SU-DHL-4 cells held in gel.

Human B cell lymphoma cells (line SU-DHL-4) were cultured in suspension using routine methodologies. Cell culture typically contain live cells and a background of dying cells, debris and occasionally non-cellular particles. In a typical analysis to distinguish objects a comparison can be made of transmission and fluorescence images. A typical methodology would comprise cell samples pre-mixed with cooled gel (24% w/v PF-127 prepared in PBS and containing 20 µM DRAQ5) and mounted under a coverslip on a cooled microscope slide. The slide was then raised to room temperature for 30 min to permit the continued in-gel staining of nuclear DNA by DRAQ5. FIG. 4 shows a typical field imaged for transmission (panel a) or far-red fluorescence of a DNA dye (DRAQ5; blue light excitation panel b). The images (see arrows) reveal the positive in-gel staining of intact cells, permitting the distinction of bi-nucleate objects (i.e. dividing cell), debris (indistinct nuclear signal) or non-cellular (non-DNA-containing) inclusions. The analysis exemplifies the imaging of non-adherent cells/objects, held in gel, enabling the sequential examination of cell/object features without loss of location in 3-dimensions.

5. Examples of the Use of Block Polymer Compositions of the Invention for Immobilizing Non-Adherent Cells for the Use High Resolution Imaging to Determine Immunofluorescence Localization.

An important feature of the PF-127 gel formulations is that they provide an easy method for immobilizing suspension cells such as those prepared for flow cytometry. This enables high resolution imaging to be performed on cells that are not originally tethered to an optical surface.

Therefore PF-127 formulations provide a route for interfacing different cytometry platforms (e.g. a flow cytometry sample analysed by imaging) particularly those that require the sequential analysis of cells in suspension. Of particular interest is the localization of a given fluorescence signal to a cellular compartment (e.g. the expression of the neural cell adhesion molecule [NCAM] on the cell surface of small cell lung carcinoma cells [SCLC cells]) or the expression of a signal in relationship to neighbouring cells where a support matrix is required to maintain a cellular cluster during, for example, multiple optical scans of a confocal or multiphoton microscope.

Here the use of gel as a support matrix for fixed cells probed with an appropriate fluorescently-tagged antibody and a DNA stain is described. NCI-H69 cells were cultured as suspension cells in RPMI-1460 culture media with 10% FCS using standard cell culture methodologies. Cells were harvested and fixed in ice-cold methanol for 20 minutes. After washing in phosphate buffered saline the samples were processed for standard immunofluorescence as used for flow cytometric analysis and fluorescence microscopy. These suspensions were prepared as flow analysis for NCAM (CD-56) detection, using mouse anti-human (CD-56; BD Pharmingen, UK) monoclonal antibody, followed by a secondary staining using an anti-mouse Alexa 488 (Molecular Probes, InVitrogen, USA). Finally the preparations were labelled with DRAQ5 to distinguish the nucleus.

A small sample of cells (50 µl at 1×106 cells per ml) was placed in a chamber coverslip (Nunc) and PF-127 sol at 24% w/v in PBS was placed over the cell layer, and left at room temperature to form a gel layer (see part A for chamber slide preparation). The cells and cell clusters became immobilized under the gel matrix.

Figure 5:
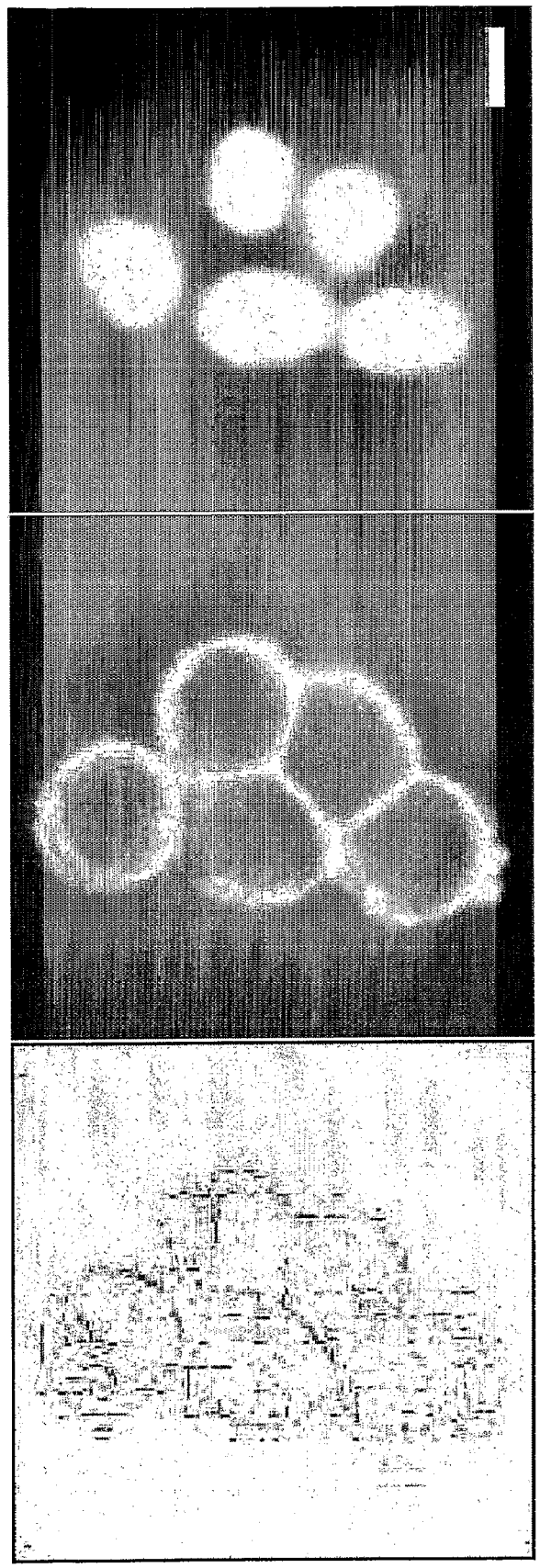
FIG. 5 shows laser scanning microscopy detection of cell nuclei and immunostaining of a cell surface antigen for fixed cells supported in gel (bar=10 μm). Left panel show transmission image, middle panel shows green Alexa 488-NCAM immunofluorescence, and the right panel shows far-red DRAQ5 nuclear fluorescence.

High resolution confocal laser scanning microscopy (Bio-Rad 1024 MP; BioRad Microscience Ltd) was performed to obtain a three channel image of the cell clump (FIG. 5). The transmission image showed optical compatibility with 488/647 nm light. The sample stability enabled imaging of the tightly coupled cells and provided distinct edges between cells depicting NCAM localization. Nuclear localization depicted the cellular localization and clearly shows the number of cells within the clump. There were no detectable background or optical scattering problems associated with the gel mountant. The example demonstrates the use of the gel with fixed cell preparations, within a protocol compatible with flow cytometric analyses and the ability high resolution immunofluorescence signals in gel.

Example III

Figure 6:
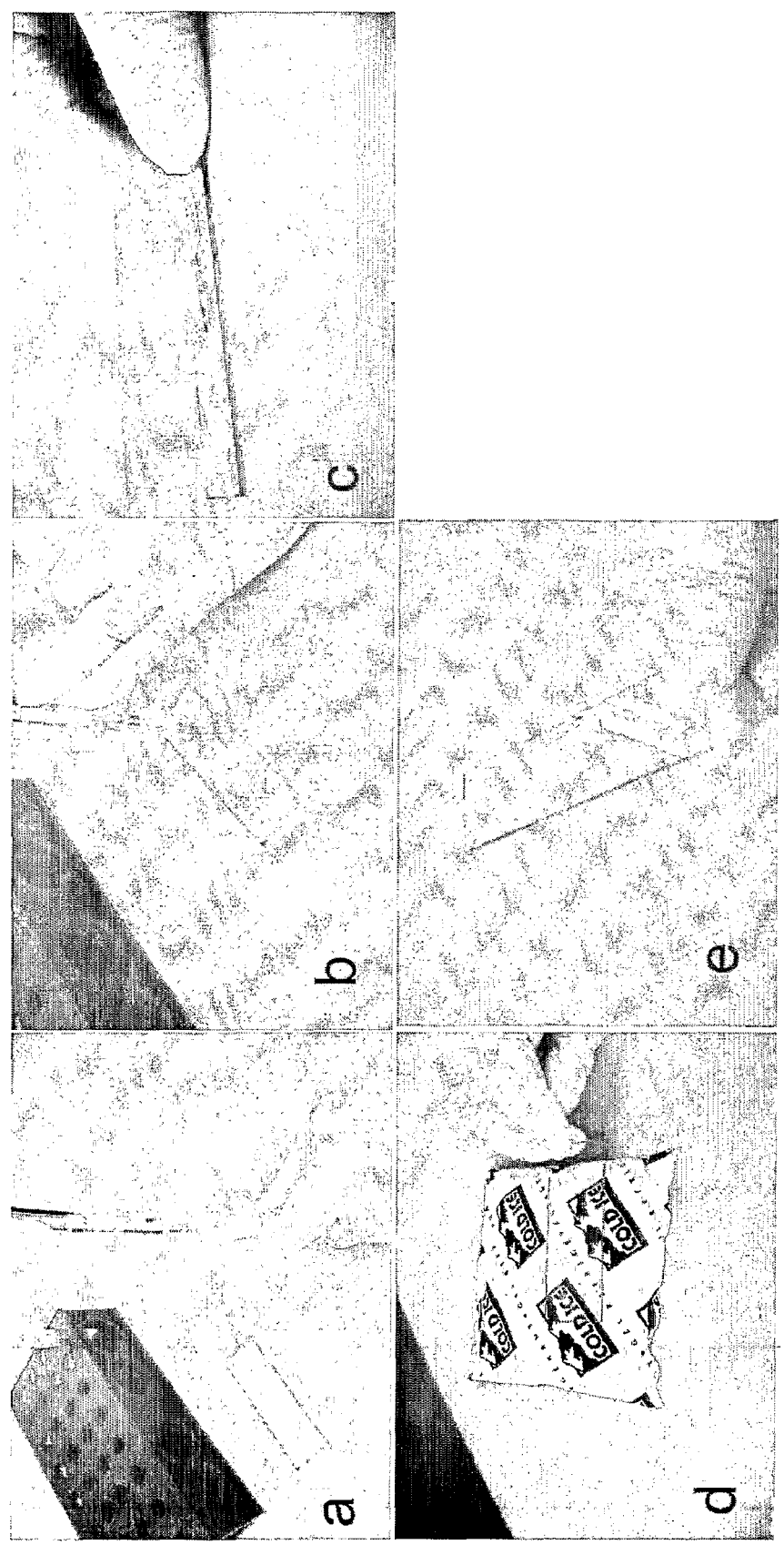
FIG. 6 shows the steps in a simple protocol to mount a sample pre-mixed in gel onto a standard microscope slide.

Examples of the Production of a Microscope Slide or Multiwell Plate Coated in a Block Polymer Composition 1. Simple Protocol to Mount a Sample Pre-Mixed in Gel onto A Standard Microscope Slide (FIG. 6 Panels a-e)

Step a: a Sample for Analysis is Mixed into Gel (in Sol Form; Held in a Sample Tube on ice) for example by the addition of a concentrated suspension of cells (e.g. $4 \times 10^5$ cells in a 10 µl volume of PBS prepared using standard centrifugation methodology) to a 250 µl volume of 24% w/v F-127 prepared in PBS). Over-strength preparations of gel can be used to provide a final concentration of 24% w/v F-127 prepared in PBS if required.

STEP b: The sample is quickly streaked across the surface of a standard microscope slide at room temperature and the gel stiffens within seconds.

STEP c: A coverslip is placed onto the gel.

STEP d: The slide is placed on an ice-pack and the gel transformed to a liquid state and spreads under the coverslip within seconds.

STEP e: Removing the slide from the ice-pack results in air-warming of the slide to room-temperature and the setting of the gel within seconds.

Figure 7:
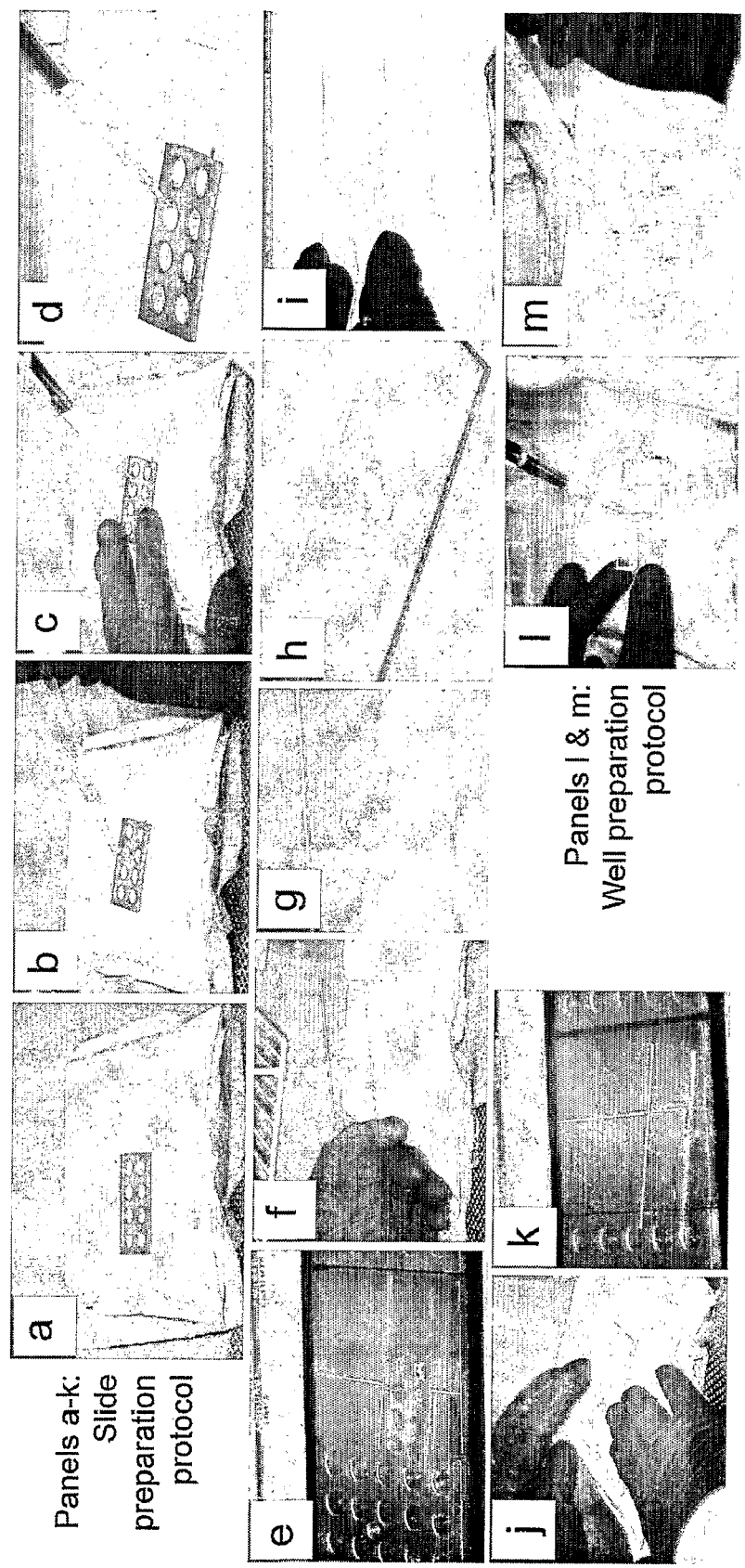
FIG. 7 shows the steps in modified protocols for the preparation of samples in gel on slides and multi-well systems.

2. Modified Protocol to Mount a Sample(s) in Gel at Given Locations on a Standard Microscope Slide (FIG. 7 Panels a-k)

Pre-prepare stained or unstained cells, beads or particles in an aqueous suspension, aspirate supernatant and hold pellet on ice. FIG. 2 (panels a-k) shows the subsequent steps for preparation of a single sample on a microscope slide, the procedure being repeated for multiple samples as required.

STEP a: Press a silicon isolator (type shown in panel a is a S2560 silicon isolator with 8 holes [each 2 mm deep, 9 mm diameter]; obtained from Sigma-Aldrich UK) onto a microscope slide on an ice-pack.

STEP b: Add 90 µL of cold 35% PF-127 gel into a well. This can be achieved, for example, using a pre-chilled 1 ml micropipette tip.

STEPS c and d: Inject the cell/bead or particle sample through the gel at the bottom of the well in a volume of 10 uL and the suspension plumes to the central area of the surface of the gel.

STEP e: Transfer slide to a warm heating block (held at 37° C.) and the gel stiffens.

STEP f: Carefully peel of the isolator.

STEP g: The gel disk revealed is self-supporting.

STEP h: Place slide onto an ice-pack until the bottom surface of the gel starts to liquefy.

STEP i: Place a coverslip onto the surface of the gel disk while the slide remains on the ice-pack. The disk continues to liquefy and starts to spread.

STEP j: Overlayer the slides with an absorbent paper and gently press to complete spreading of the sample and to remove excess liquid.

STEP k: Return to warm heating block to stiffen gel and complete preparation. Return to room temperature for storage (e.g. up to 24 h).

3. Modified Protocol to Mount a Sample in a Chamber/Well (e.g. Standard Glass Bottom 8 Well Chamber Slide) (FIG. 7 Panels l & m)

Pre-prepare stained or unstained cells, beads or particles in an aqueous suspension, aspirate supernatant and hold pellet on ice. The procedure for the addition of the gel and sample is reversed from that described above. FIG. 2 shows the main steps of introducing the cell/bead or particle sample in a volume of 10 µL into an empty well/chamber of a multi-chamber slide held on an ice-pack (panel l). Then add 90 uL of cold 35% PF-127 gel into the well (panel m). This can be achieved, for example, using a pre-chilled 1 ml micropipette tip. The liquid gel overlayers the sample suspension. The slide is then warmed (e.g. on a heating block at 37° C.) to stiffen the sample-gel interface, as described above, prior to analysis.

4. Simple Exemplar Protocol for the Preparation of Dried Films of Block Polymer and their Reconstitution in a Multi-Well Plate (Table 3)

An example of a methodology is described for the preparation of dried films of PF-127 and their reconstitution by the addition of differing volumes of water (or a given solution) to provide a range of potential gel/liquid concentrations for cell/bead or particle immobilisation or manipulation. The steps are outlined below.

STEP a: A 19.3% w/v PF-127 solution in water was prepared. This concentration permits a liquid state to be easily formed when chilled (e.g. at 4° C.) but still retain some degree of loose gel/liquid state at room temperature (20° C.).

STEP b: Volumes of cold gel were dispensed into a matrix of 48 wells within a standard 96-well (flat bottomed) transparent plastic dish as indicated in the Table.

STEP c: The plate was held on a heating block at 37° C. for 24 h to allow for the desiccation of the gel into dried films covering the base of each well. Here the process may be accelerated for example by vacuum drying.

STEP d: At this stage the dried films can be stored before commitment to rehydration.

STEP e: Volumes of ice-cold PBS are dispensed into each well as indicated in the Table and the plate rotated briefly to aid the wetting of the dried. Here the process may be accelerated by mechanical vibration.

STEP f: The plate is then held with the lid sealed for 24 h at 4° C. Here the rehydration conditions may be varied (e.g. incubating at 37° C. in a humidified atmosphere).

STEP g: After rehydration the plate is returned to room temperature for the assessment of quality gel formation in the wells by direct and microscopic examination of the transparency and the mechanical properties by agitating the well contents with a pipette tip.

Results: Table 3 shows the ability to prepare liquid and gel-like phases in all combinations when assessed at room temperature. Here reconstitution was achieved using PBS demonstrating the in situ preparation of gels with a buffer of choice. Some wells showing liquid phase (i.e. 'liquid') at room temperature would be capable of forming gels if the temperature was raised. Further, only some combinations resulted in the formation of a transparent and optically acceptable gel (i.e. 'transp. gel') with in other case a turbid-opaque gel/paste formed (i.e. 'gel'). The combination of a 75 µL 19.3% PF-127 dried gel film reconstituted with a 50 µL PBS volume provided a transparent gel (reversible to a sol by chilling) with a nominal poloxamer concentration of 29%. This preferred combination would allowing for the retention of room temperature (and 37° C.) immobilisation properties and permit the further addition of sample volumes upon (for example reducing the final concentration of gel to 24%).

TABLE 3

Reconstitution of dried films of PF-127 (19.3% w/v gel in water) and the effects of reconstitution with differing volumes of PBS

| µL gel dried: | Dried gel reconstituted with PBS (µL) | | | | | |
|---|---|---|---|---|---|---|
| | 10 | 25 | 50 | 100 | 150 | 200 |
| 10 | trans. gel | liquid | liquid | liquid | liquid | liquid |
| 20 | trans. gel | trans. gel | liquid | liquid | liquid | liquid |
| 25 | trans. gel | liquid | liquid | liquid | liquid | liquid |
| 50 | trans. gel | liquid | liquid | liquid | liquid | liquid |
| 75 | trans. gel | trans. gel | trans. gel | liquid | liquid | liquid |
| 100 | gel | trans. gel | trans. gel | liquid | liquid | liquid |
| 150 | gel | gel | gel | liquid | liquid | liquid |
| 200 | gel | gel | gel | trans. gel | liquid | liquid |

Example IV

Example of the Production of a Block Polymer Composition Comprising Fluorescent Beads and/or a Dye

Figure 8:
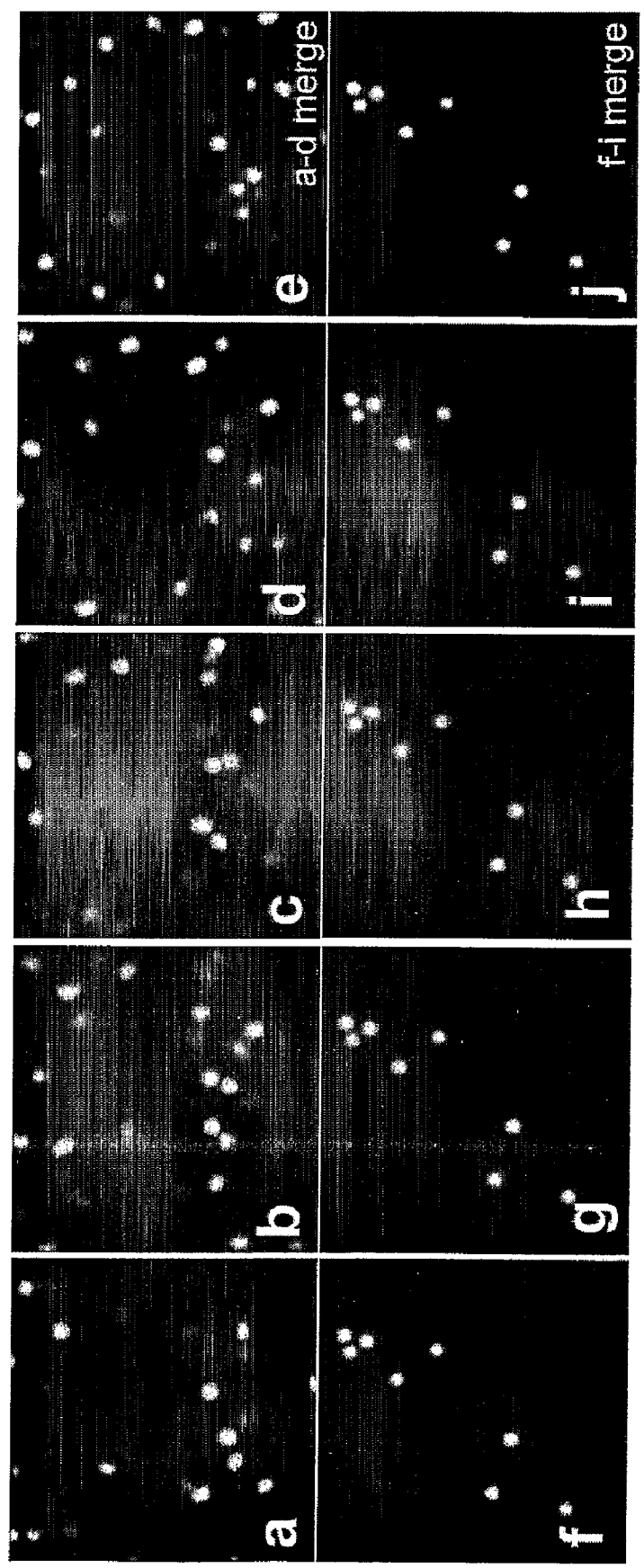
FIG. 8 shows time-lapse imaging of beads in PBS or gel reveals efficient trapping of fluorescent objects for sequential image collection.

1. Simple Protocol to Prepare Fluorescent Beads in a Gel for the Purpose of Immobilisation and Analysis Analysis of beads may, for example, require the determination of bead location and optical properties such as fluorescence. An example of a typical protocol for the analysis of fluorescence characteristics and bead location is shown in FIG. 8 for red-fluorescent approx. 1 µm diameter beads (e.g. Becton Dickinson Calbrite APC beads; BD Biosciences, USA) using excitation and emission conditions described by the manufacturer. The general methodologies for preparing beads in gel have been described above. A concentrated preparation of beads (e.g. 1 drop into 0.5 ml gel and mixed on ice using a pipette micro-tip. A gel sample was prepared on a microscope slide. A time-lapse imaging system described above was used to sequentially image the fluorescence of beads either in PBS (as a film trapped under a coverslip) or in 24% w/v gel (PF-127 prepared in PBS). Images a to d shows the same field of view for beads in PBS, imaged 4 times with a 1 sec interval between each image capture. Image e shows the 4 merged images of a-d. Similarly, images f-i show 1 sec interval images for beads in gel at room temperature with the corresponding merged image shown in panel j. The beads clearly move in the PBS preparation, due to fluid movement and Brownian motion, resulting in a confused merged image. Beads remain at fixed locations in the gel for the scanning period demonstrating the immobilization properties of the gel for beads.

Figure 9:
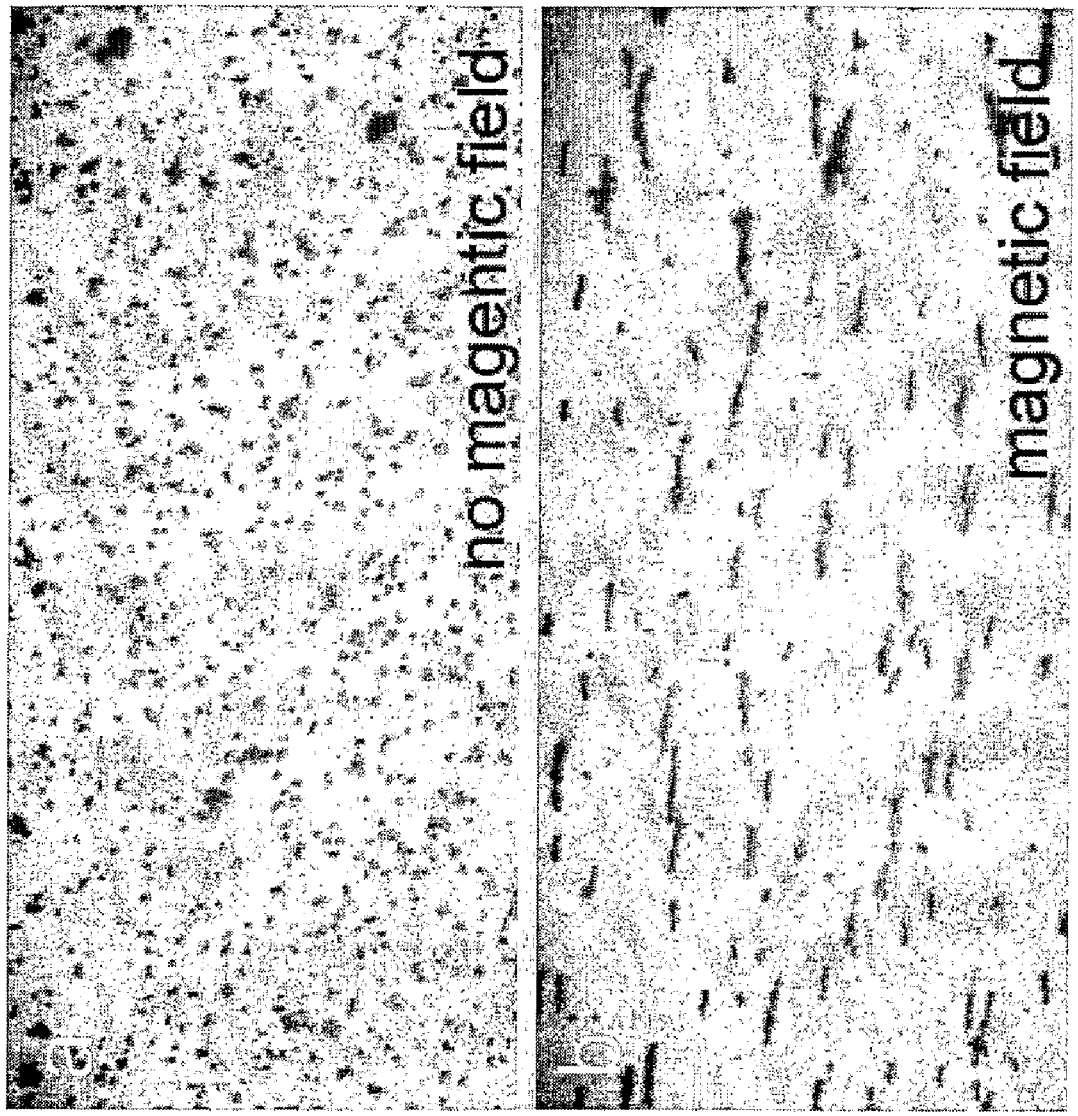
FIG. 9 shows the effects of a magnetic field on dispersed magnetic beads in a 24% PF-127 gel at room temperature.

2. Simple Protocol for the Preparation of Magnetic Beads in Gel and their Manipulation in a Magnetic Field Magnetic bead technology is in common use for separation methodologies. Unlabelled magnetic beads (obtained from The Reagent Mine Ltd., Melton Mowbray, UK; approx 2 µm diameter) were dispersed into gel (24% w/v PF-127 prepared in water) at 4° C. in a 2 mL polypropylene sample tube. The suspension was then prepared on a microscope slide for imaging by transmitted light using a standard microscope equipped with a camera system. FIG. 9 (panel a) shows the dispersed beads immobilized in gel at room temperature. A neodymium magnet (The Reagent Mine Ltd., Melton Mowbray, UK) was then placed 2.5 cm from the centre of the field of view and the same height as the slide surface and after 30 seconds the field re-imaged. FIG. 9 (panel b) shows the effect of the magnetic field resulting in bead alignment along the lines of force, demonstrating the ability to move beads in a supporting gel for the purposes of alignment and re-location within the gel.

3. Preparation of a Dye in Gel

Figure 10:
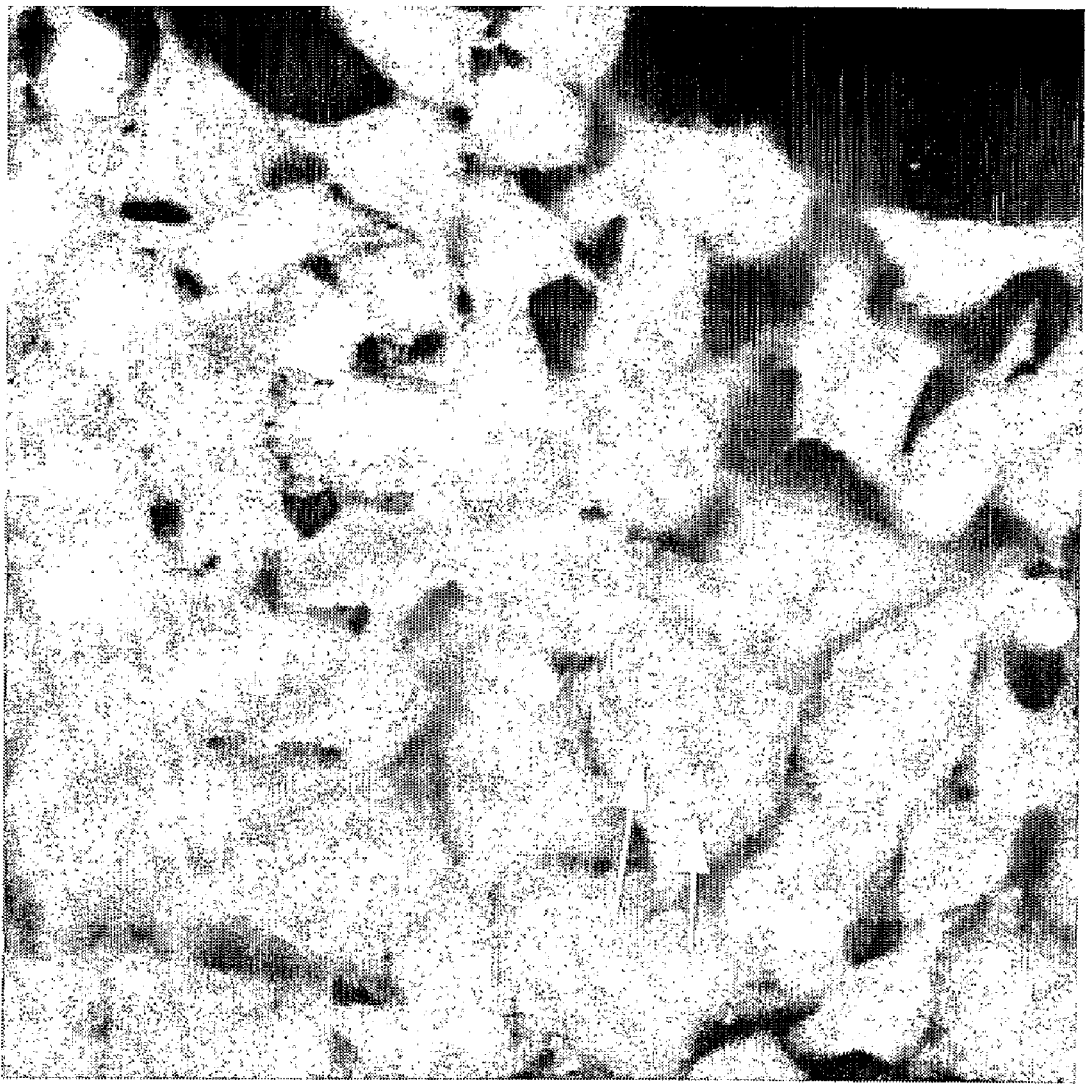
FIG. 10 shows typical results for calcein loaded cells (MCF-7 human breast carcinoma cells cultured using routine methodologies in glass-bottomed chambers and using a camera-based system.

Vital-labelling methodologies often require the uptake of a non-fluorescent form of a dye which becomes fluorescent upon intracellular processing. Here the preparation of the vital dye calcein-AM is described for the in-gel staining of live cells overlayered with the gel-dye preparation. Calcein dye (calcein AM; 0.1 µg/ml; C3099 Cat. No., Molecular Probes, InVitrogen) was mixed into a 24% w/v PF-127 prepared in PBS and overlayered onto a monolayer culture of human MCF-7 cells in a chamber slide and incubated at room temperature for 15 min. Images were collected using standard confocal microscope methodologies (system: BioRad 1024 MP, BioRad Microsciences, UK). FIG. 10 shows an optical section through cells demonstrating a typical compartmentalization of the dye in some cells with more diffuse staining in others. The results demonstrate the ability to prepare a dye in gel for live cell marking and function.

Example V

Examples of the Use of Block Polymer Compositions of the Invention in the Calibration of Equipment for Optical Analysis (E.G. the Determination of Point Spread Function)

1. Gel Preparations Used for Immobilization have Advantageous

Imaging instruments (microscopes and HCS instruments) produce a spatially sampled array of fluorescence. Images may be produced by the optical system directly (camera-based) or built up by scanning (laser scanning microscope). Fewer changes in refractive index at the different optical interfaces are advantageous. The availability of aqueous-based gels provides an advantageous medium in terms of refractive index when compared, for example, with higher RI glycerol-based mountants. Standard refractometry was used to measure the RI values for typical gel preparations and the values obtained are shown in Table 4.

TABLE 4

Typical values for refractive index obtained for gel preparations

| Sample | Refractive index (RI) |
|---|---|
| PF-127 24% w/v prepared in water; at 37° C. | 1.357 |
| PF-127 24% w/v prepared in PBS; at 37° C. | 1.359 |
| PBS | 1.333 |
| water | 1.331 |

Spatial resolution in theory: Illumination wavelengths (from an arc lamp) are selected by an excitation filter or spectrometer and the light is spread onto a field aperture by a high Numerical Aperture condenser lens. It then reflects from a 45 degrees dichroic mirror and an image of the field aperture is demagnified into the sample by an objective lens. In this way, the entire sample is evenly bathed in light. Fluorescence is collected by the objective and forms an image in the microscope that is either inspected visually, using a magnifying eyepiece, or passed to an appropriate photo-detector such as a CCD camera. All parts of the illuminated sample contribute to the image that contains sharp (in focus) features as well as out-of focus features. It is important to consider the performance characteristics of any fluorescence imaging instruments. An image of a sub-resolution fluorescent bead (i.e. smaller than about 200 nm) will show an airy disk consisting of a central spot surrounded by faint light and dark rings. Measurement of the airy disk gives parameters describing the microscope performance. The distance from the centre to the first dark ring describes horizontal (x, y) resolution and is given by:

$$dxy = 0.61 \lambda / NA$$

If a focus series of images of the bead is collected, the corresponding axial (z) resolution is:

$$dz = 3.7 dxy \eta / NA$$

η=refractive index of sample medium
λ=wavelength
NA=objective lens Numerical Aperture Total intensity in any horizontal plane is proportional to NA2/(magnification) and is constant near the focus, so there is no optical sectioning in a conventional microscope.

Spatial resolution in practice: The rigor in which an assay can be implemented on any imaging system is dependent on reproducibility and calibration of the instrument. It is essential to understand the spatial performance of the imaging system in order to extract quantitative information or indeed undertake deconvolution processing to extract 3D information. Since the refractive index of the sample medium linearly influences axial resolution and the axial performance changes is depth due to spherical aberration it is important to calibrate the axial resolution 'in situ'. The accepted method for obtaining the x,y,z performance of a microscope is to acquire image from a sub-resolution bead in the exact same conditions used for imaging the sample. However in water-based samples (physiological buffers and media) it is essential to keep the cells living and acquire xyz calibration information from a bead. By placing the sample (cells) and beads in block polymer compositions high resolution images of immobilized beads can be obtained enabling axial performance to be extracted.

To exemplify the use of block polymer compositions with integrated sub-resolution beads we are able to obtain information on the optical performance of the instrument at different depths through the sample.

Materials and Sample Preparation:

(i) Sub-resolution beads can be obtained from many different manufacturers in this case Molecular Probes. PS-speck Microscope point Source Kit: 505/515 nm fluospheres carboxylate modified microspheres 0.17 µm yellow-green fluorescent (concentration 107 per ml).

(ii) Block polymer composition (PF-127) at a formulation of 24% w/v in water was prepared as previously described above.

Step 1: Take 0.5 mls of 24% Pluronic® F127 maintained at 4° C. and mix with 5 µl bead solution.

Step 2: Maintain at 4° C. on ice until ready to use

Step 3: Place 50 µl on to a microscope slide (the droplet becomes gel)

Step 4: Place a coverslip (22 mm×22 mm) onto the droplet

Step 5: Cool the slide on an ice block and the droplet spreads and the coverslip becomes level.

Obtaining a focus series of images through the bead along the optical axis (see figures)

Step 1: Firmly secure the slide to the microscope (vibrations will disturb image collection)

Step 2: Choose the appropriate imaging conditions to obtain the focus series.

Figure 11:
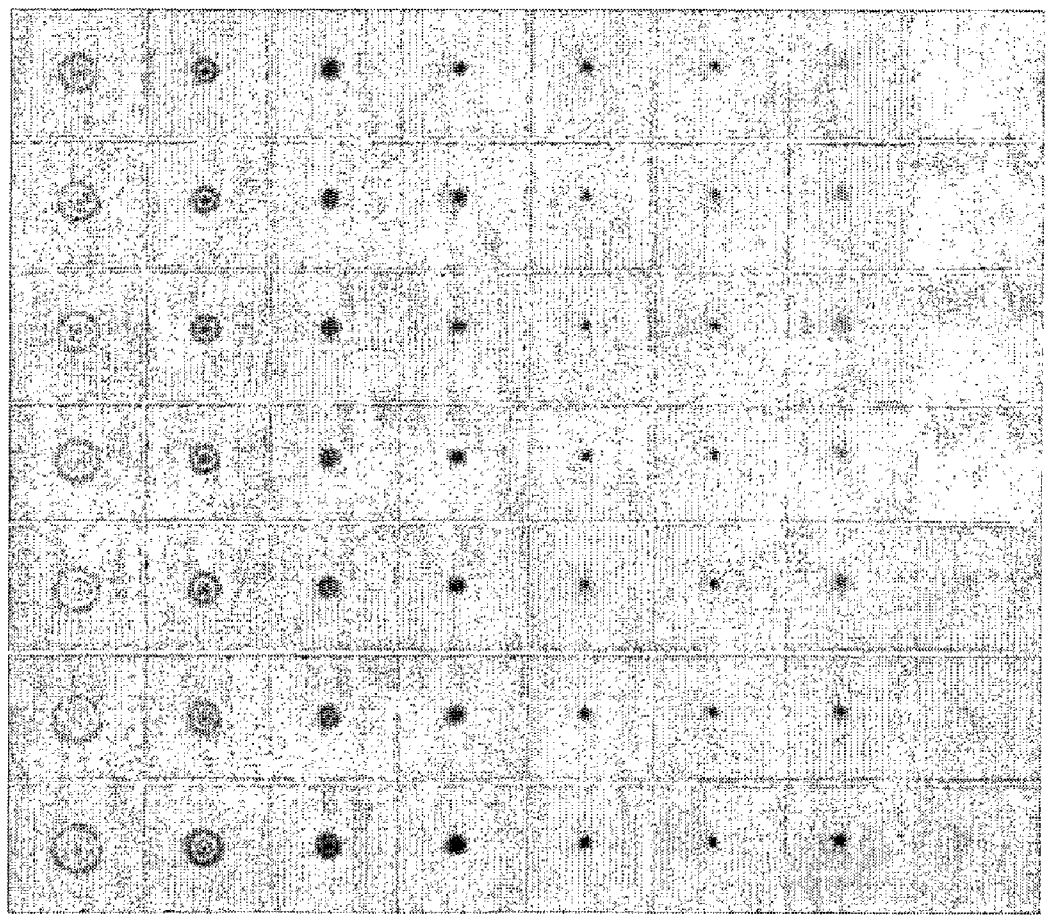
FIG. 11 shows a wide-field (CCD-camera) focus series through a 170 nm bead mounted in PF-127 24% w/v in water (inverted contrast). The slide was mounted onto a Nikon fixed stage upright microscope, and imaged using a x40 ELWD NA 0.6 air objective lens (pixel resolution of 0.23 μm). In fluorescence mode (470/40 excitation and 525/50 emission) a focus series was collected using z-steps of 0.15 μm a total of 51 planes were captured which is an equivalent of 7.5 μm total distance. A single bead was cut out of the total stack and was montaged to show the diffraction rings. An image of a sub-resolution fluorescent bead (i.e. smaller than about 200 nm) showed an airy disk consisting of a central spot surrounded by faint light and dark rings.
Figure 12:
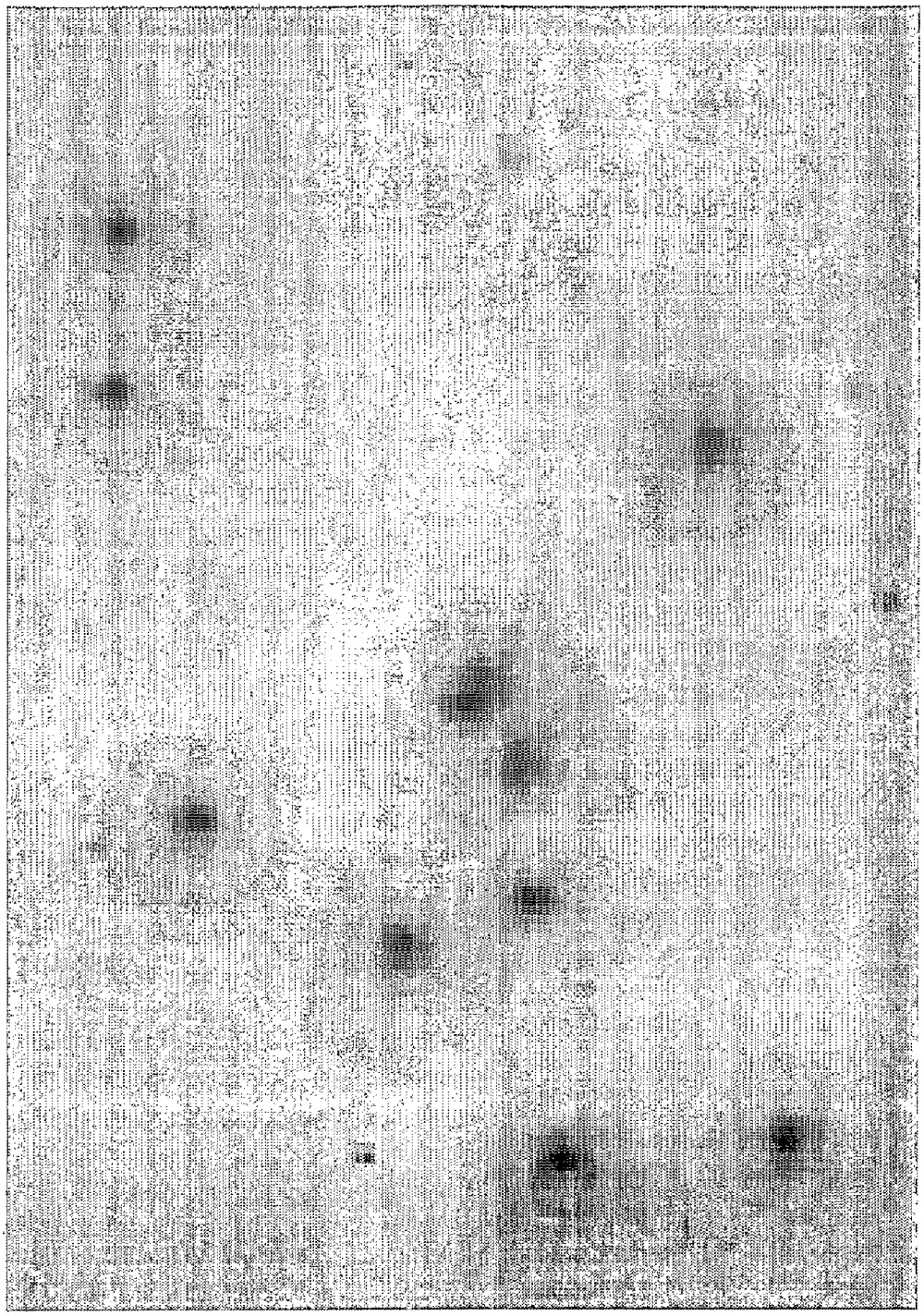
FIG. 12 shows the maximum projection of a focus series through a 170 nm bead mounted in PF-127 24% w/v in water (inverted contrast). The conditions were identical to those described above. The beads remain stationary throughout the entire series which took approximately 3 minutes to collect. Each bead consists of a bright (black) centre and rings around the centre; showing that each of the beads is stationary.
Figure 13:
FIG. 13 shows two typical wide field point spread functions (PSF) obtained by resampling the data in xz. The asymmetric image arises due to spherical aberrations (i.e. an air lens (refractive index looking into a 24% PF-127 gel sample refractive index 1.357). This is a typical situation in high content screening instruments screens where air lenses are used routinely, while the live sample sits in gel within a multiwell plate. The PSF sits at a slight slant due to the fact that the alignment of the instrument is slightly out and off axis. Taken together the bead images provide a quantitative evaluation of the instrument performance in conditions identical to those used for a typical live cell multi-well imaging setup. Immobilising beads in media or physiological buffer only for this kind of evaluation would not be possible.

Results are shown in FIGS. 11 to 13.

Reference

White N S, Errington R J. *Fluorescence techniques for drug delivery research: theory and practice*. Adv Drug Deliv Rev. 2005 Jan. 2; 57(1):17-42.

Example VI

Figure 14:
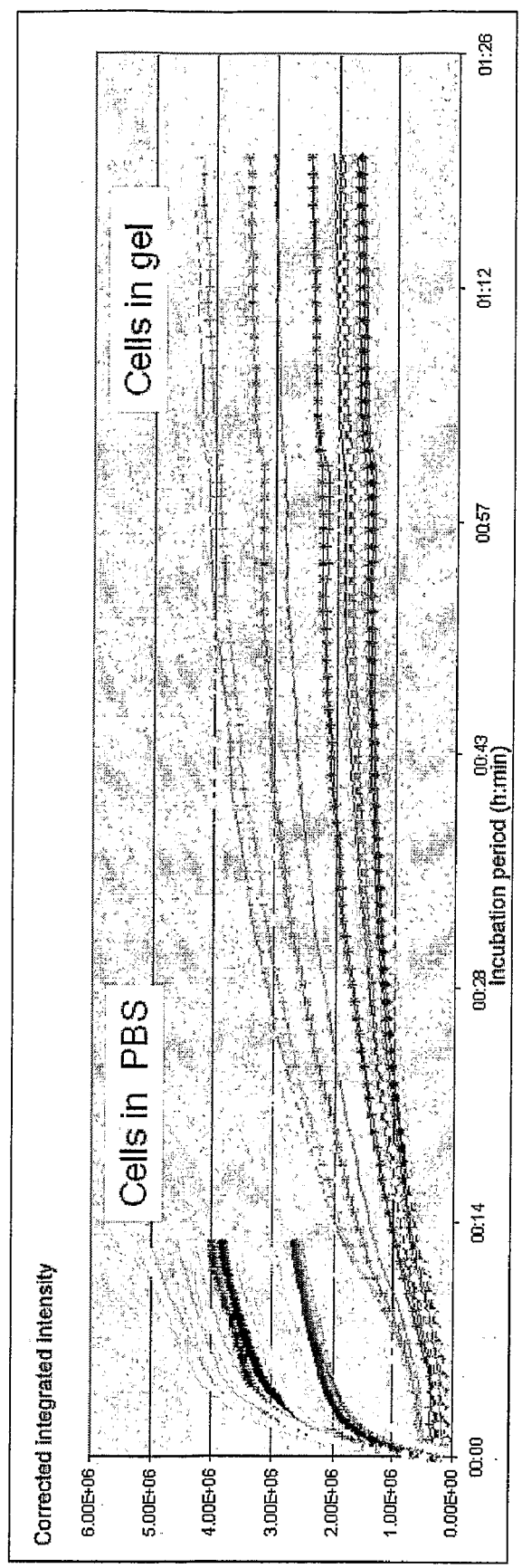
FIG. 14 shows a comparison of the kinetics of uptake of DRAQ5 dye into U2-OS human tumour cells held in PBS or gel

Examples of the Use of Block Polymer Compositions of the Invention in the Controlled Delivery of Reagents to Cells 1. Delivery of a Cell-Permeant DNA Dye to Cells in Gel The delivery of reagents to cell, beads or particles immobilized in gel permits the analysis of modified interaction kinetics over extended periods. Described herein is an example of the impact of gel-based delivery of a reagent, cell permeant DNA dye DRAQ5, in comparison with the kinetics obtained by the staining in PBS alone. Here attached U-2 OS (American Type Culture Collection [ATCC] HTB-96) cells were grown in glass-bottomed chamber slides using standard cell culture methodologies. The use of attached cultures allowed for their immobilization for staining in PBS and a direct comparison with the staining in gel. The culture medium was aspirated and replaced with either PBS supplemented with DRAQ5 (20 μM) or overlayered with gel (24% w/v PF-127 prepared in PBS) also containing DRAQ5 (20 μM). Samples were then imaged using a time-lapse microscope and the changes in nuclear associated far-red fluorescence monitored in individual cells analysed. FIG. 14 shows the uptake kinetics in PBS versus gel for individual cells. The well recognised asynchronous nature of cell cultures under normal growth conditions results in a range (2-fold) of cellular DNA contents representing the cell cycle age distribution of the population. In PBS there is a rapid staining of cells with the expected spread in near-equilibrium values for nuclear fluorescence intensity. In gel staining also re-iterates the spread in values but with slower kinetics (>10-fold) as expected from a gel-diffusion limited staining of cells.

2. Differential Staining of Live and Dead Cells in Gel Using a Fluorescent Dye

Figure 15:
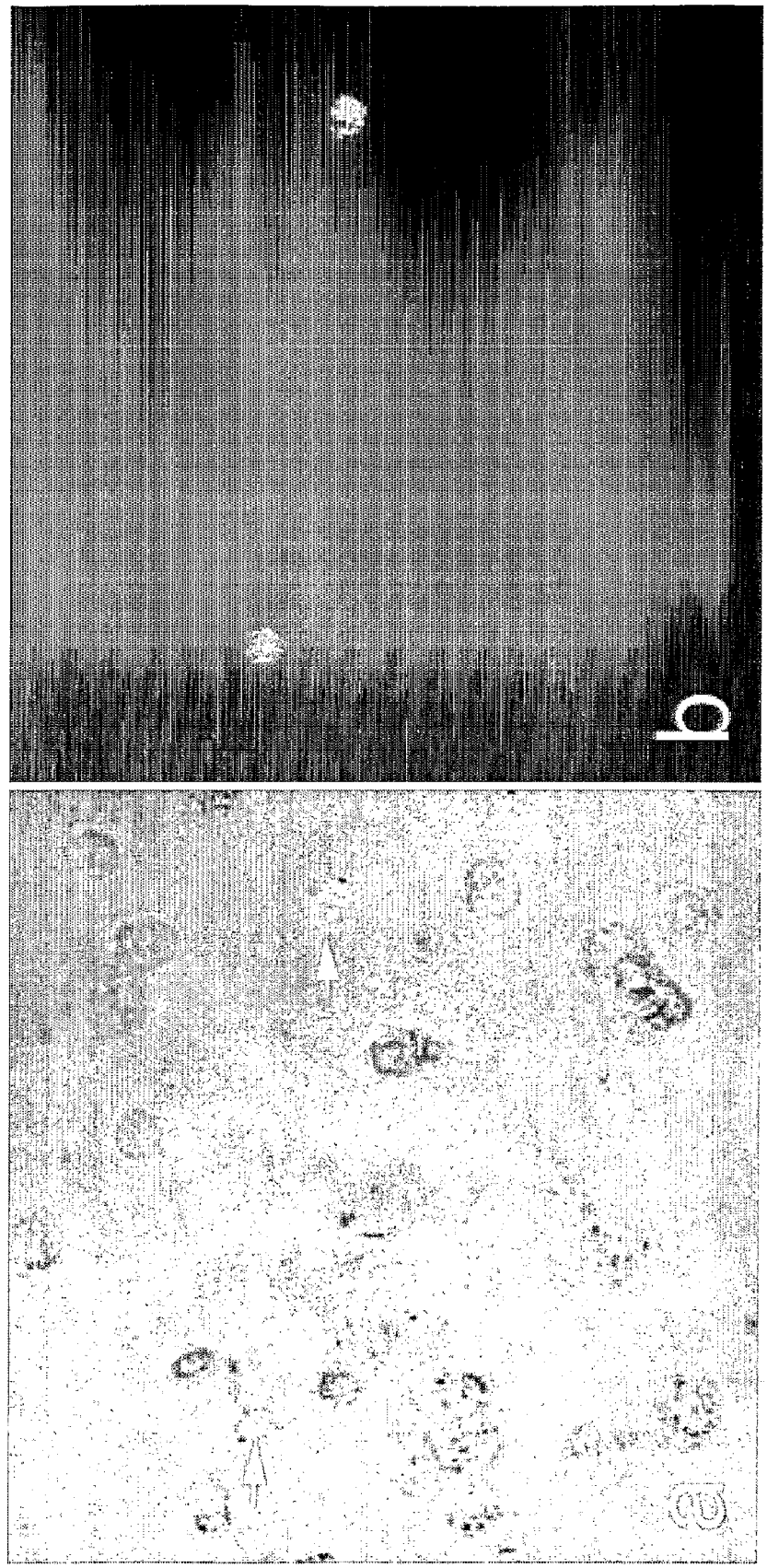
FIG. 15 shows differential staining of live and dead (arrowed) human B cell lymphoma cells viewed by transmission (panel a) or fluorescence of nuclei of cells stained with propidium iodide.

In FIG. 15, propidium iodide (PI) enters into damaged cells (undergoing cell death) due to the inability of damaged plasma membranes to exclude the cationic dye. Intact healthy cells do not stain if membrane integrity is preserved. A typical analysis for live/dead cell discrimination in gel is described here. DoHH2 (human B cell lymphoma cells) cell line has a normal background of apoptotic (dying) cells that are normally distinguishable by there positive staining using PI. FIG. 2 shows a comparison of the transmission and red-fluorescence images, upon blue light excitation, of cells held and stained in gel (24% w/v PF-127 prepared in PBS; containing 1 μg/ml propidium iodide) at room temperature for 15 min. There is the clear ability to distinguish positive and negative staining cells showing that gel delivery of a reagent can be used for the purpose of event discrimination.

The invention claimed is:

1. A method for analyzing particles comprising immobilizing the particles in a composition comprising a block copolymer and analyzing the immobilized particles.

2. The method of claim 1, wherein the composition exhibits the following properties: gel-sol thermoreversibility; micelle formation under gelling conditions; compatible with light-based optical assays in the electromagnetic spectrum of 350 to 1300 nm; controllable surfactant properties; molecular sieving properties; and substantially non-cytotoxic.

3. The method of claim 2, wherein the block copolymer is present in the composition at a gelling concentration.

4. The method of claim 1 wherein the particles are derived from or constitute a biological sample.

5. The method of claim 1, wherein the particles are cells.

6. The method of claim 5, wherein the cells are fixed.

7. The method of claim 5, wherein the cells are live.

8. The method of claim 5, wherein the cells are non-adherent.

9. The method of claim 5, wherein the cells are selected from the group consisting of human cells, animal cells, cultured cell lines, immortal somatic cell hybrids, yeast cells, plant cells and fungal cells.

10. The method of claim 5, wherein the cells are capable of expressing a fluorescent molecule.

11. The method of claim 1, wherein the particles are fluorescent beads.

12. The method of claim 1, wherein the block copolymer is a block copolymer of polyoxyethylene and polyoxypropylene.

13. The method of claim 12, wherein the block copolymer is selected from the group consisting of poloxamer 407, poloxamer 338, poloxamer 288, poloxamer 237, poloxamer 238, poloxamer 217, poloxamer 188 and poloxamer 108.

14. The method of claim 1, wherein the composition is applied to a surface of a microscope slide, a coverslip or a multichamber plate.

15. The method of claim 1, wherein the composition serves as a support matrix for the analysis of particles involving light collection.

16. The method of claim 15, wherein the light is fluorescence, bioluminescence or chemoluminescence.

17. The method of claim 1, wherein the composition serves as a support matrix for the analysis of particles by imaging, microscopy or non-imaging plate based assays.

18. The method of claim 1, wherein the analysis is for calibration, optical alignment or orientation in methodologies requiring the collection of light.

19. The method of claim 1, wherein the analysis is for calibration, point-spread function determination and event orientation within optical slices of two or more dimensions.

20. The method of claim 1, wherein the composition further comprises fluorescent beads.

21. The method of claim 1, wherein the composition further comprises a dye.

22. The method of claim 21, wherein the dye is a DNA fluorochrome.

23. The method of claim 21, wherein the dye is 1,5-bis{[2-(methylamino)ethyl]amino}-4,8-dihydroxy anthracene-9,10-dione.

24. The method of claim 1, wherein the particles are encapsulated in the composition comprising a block copolymer.

25. The method of claim 1, wherein the method is for multidimensional analysis of particles.

26. The method of claim 25, wherein the multidimensional analysis is selected from the group consisting of 3D(x,y,z) imaging, time (kinetic) analysis and lambda (spectral) analysis.

27. The method of claim 1, wherein the analysis is performed by high throughput screening.

28. The method of claim 1, wherein the composition comprising a block copolymer provides a means of controlling or modifying access of reactants and reporter molecules to the particles.

* * * * *